(12) United States Patent
Guss et al.

(10) Patent No.: US 6,733,758 B1
(45) Date of Patent: May 11, 2004

(54) FIBRINOGEN BINDING PROTEIN ORIGINATING FROM COAGULASE-NEGATIVE STAPHYLOCOCCUS

(76) Inventors: Bengt Guss, Dag Hammarskjölds Väg 238B, S-756 52 Uppsala (SE); Martin Nilsson, Dragarbrunnsgatan 60, S-752 30 Uppsala (SE); Lars Frykberg, Stabby Alle 7C, S-752 29 Uppsala (SE); Jan-Ingmar Flock, Sångarvägen 2, S-161 28 Bromma (SE); Martin Lindberg, Inst. För Mikrobiologi, P.O. Box 7025, S-750 07 Uppsala (SE)

( * ) Notice: Subject to any disclaimer, the term of this patent is extended or adjusted under 35 U.S.C. 154(b) by 0 days.

(21) Appl. No.: 09/147,405

(22) PCT Filed: Jun. 18, 1997

(86) PCT No.: PCT/SE97/01091

§ 371 (c)(1),
(2), (4) Date: Apr. 1, 1999

(87) PCT Pub. No.: WO97/48727

PCT Pub. Date: Dec. 24, 1997

(30) Foreign Application Priority Data

Jun. 20, 1996 (SE) .................................. 9602496

(51) Int. Cl.⁷ ...................... A61K 30/085; A61K 39/02; A61K 39/00; C07K 1/00
(52) U.S. Cl. ................................ 424/243.1; 424/237.1; 424/234.1; 424/184.1; 424/190.1; 424/192.1; 530/350; 530/300; 530/825; 514/2
(58) Field of Search .......................... 424/237.1, 243.1, 424/244.1, 192.1; 530/412, 350, 300

(56) References Cited

U.S. PATENT DOCUMENTS 5,055,455 A * 10/1991 Pier
5,587,307 A * 12/1996 Alborn et al. ........... 435/240.1
6,107,068 A * 8/2000 Katz et al. ................. 435/189

FOREIGN PATENT DOCUMENTS

| DE | 03583987 | * | 10/1985 |
| EP | 350810 | * | 1/1990 |
| WO | WO 9406830 A1 | | 3/1994 |

OTHER PUBLICATIONS

McDevitt et al. Mol. Microbiol. 11: 237–248, 1994.*
Marston et al. In: Methods in Enzymology, Guide to Protein Purification. (Ed) MP Deutscher. Vol. 182, section 20, pp. 264–276, 1991.*
Usui Y. Zbl. Bakt. Hyg. A 262: 287–297, 1986.*
Timmerman et al Infection and Immunity 59(11) 4187, Abstract only, 1991.*
Dialog Information Services, file 155 (Zentralbl Bakteriol Mikrobiol Hyg., 262(3):287–297 (1986).
Dialog Information Services, file 5, Holzhueter et al., Vweh Dtsch Ges Inn Med., 79:1325–1327 (1974).
McDevitt et al., Molecular Microbiology, 11(2):237–248 (1994).

* cited by examiner

*Primary Examiner*—S. Devi
(74) *Attorney, Agent, or Firm*—Bacon & Thomas

(57) ABSTRACT

A new fibrinogen binding protein or polypeptide originating from coagulase negative staphylococci, biotechnological methods for producing the protein or polypeptide having fibrinogen binding activity and a recombinant DNA molecule coding for the protein (or fragments thereof), and micro-organisms (including viruses) containing this recombinant DNA molecule. The present invention further comprises the therapeutic and diagnostic use of the protein and/or DNA, e.g., a diagnostic kit for determining the presence and/or type of coagulase negative staphylococci and a vaccine composition, comprising the protein or DNA.

4 Claims, 15 Drawing Sheets

Fig. 6A

Figure 1:
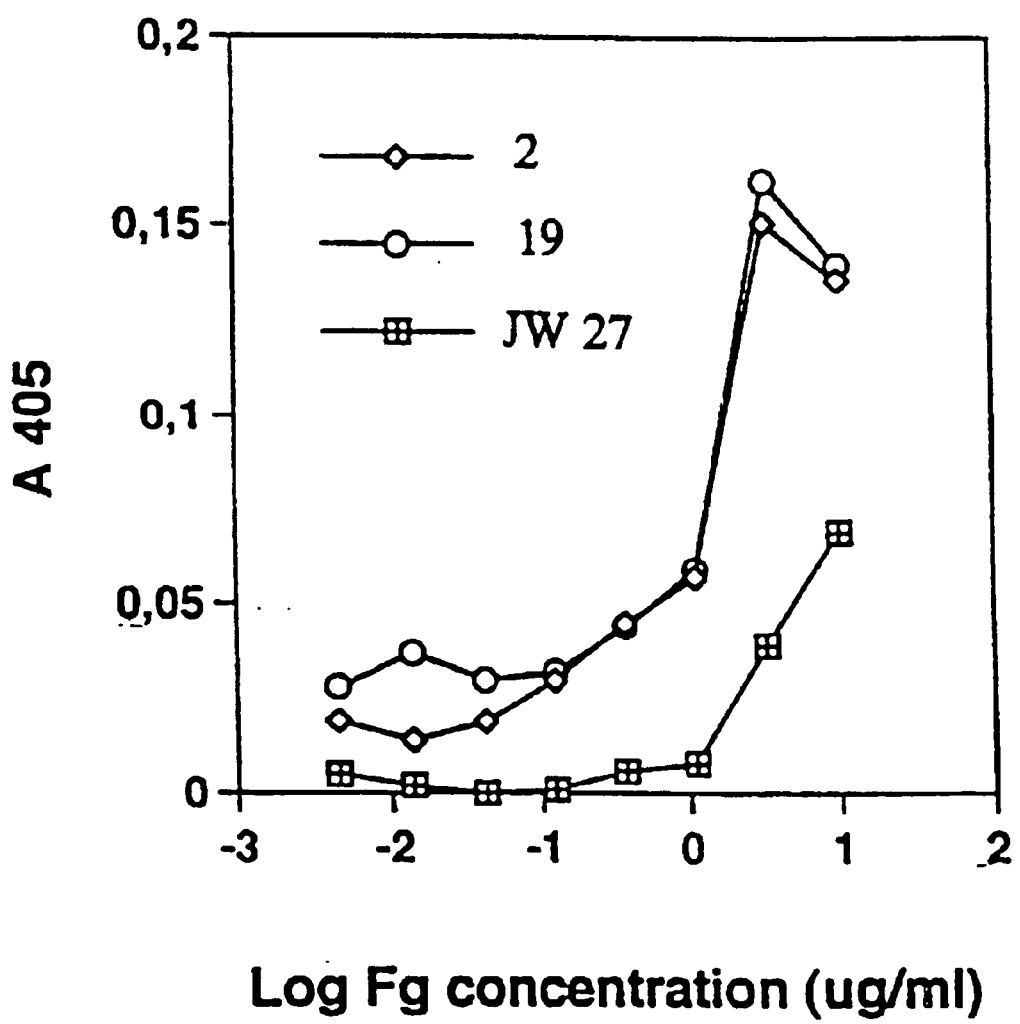

```
                          →S
TACATTGAAATAGTCAAAGAAAAGGAGTTTTTATGATTAATAAAAAAAATAATTTACTAA-60
                                  M  I  N  K  K  N  N  L  L  -9

CTAAAAAGAAACCTATAGCAAATAAATCCAATAAATATGCAATTAGAAAATTCACAGTAG-120
 T  K  K  K  P  I  A  N  K  S  N  K  Y  A  I  R  K  F  T  V  -29

GTACAGCGTCTATTGTAATAGGTGCAACATTATTGTTTGGTTTAGGTCATAATGAGGCCA-180
 G  T  A  S  I  V  I  G  A  T  L  L  F  G  L  G  H  N  E  A  -49

→A
AAGCCGAGGAGAATTCAGTACAAGACGTTAAAGATTCGAATACGGATGATGAATTATCAG-240
 K  A  E  E  N  S  V  Q  D  V  K  D  S  N  T  D  D  E  L  S  -69

ACAGCAATGATCAGTCTAGTGATGAAGAAAAGAATGATGTGATCAATAATAATCAGTCAA-300
 D  S  N  D  Q  S  S  D  E  E  K  N  D  V  I  N  N  N  Q  S  -89

TAAACACCGACGATAATAACCAAATAATTAAAAAAGAAGAAACGAATAACTACGATGGCA-360
 I  N  T  D  D  N  N  Q  I  I  K  K  E  E  T  N  N  Y  D  G  -109

TAGAAAAACGCTCAGAAGATAGAACAGAGTCAACAACAAATGTAGATGAAAACGAAGCAA-420
 I  E  K  R  S  E  D  R  T  E  S  T  T  N  V  D  E  N  E  A  -129

CATTTTTACAAAAGACCCCTCAAGATAATACTCATCTTACAGAAGAAGAGGTAAAAGAAT-480
 T  F  L  Q  K  T  P  Q  D  N  T  H  L  T  E  E  E  V  K  E  -149

CCTCATCAGTCGAATCCTCAAATTCATCAATTGATACTGCCCAACAACCATCTCACACAA-540
 S  S  S  V  E  S  S  N  S  S  I  D  T  A  Q  Q  P  S  H  T  -169

CAATAAATAGAGAAGAATCTGTTCAAACAAGTGATAATGTAGAAGATTCACACGTATCAG-600
 T  I  N  R  E  E  S  V  Q  T  S  D  N  V  E  D  S  H  V  S  -189

ATTTTGCTAACTCTAAAATAAAAGAGAGTAACACTGAATCTGGTAAAGAAGAGAATACTA-660
 D  F  A  N  S  K  I  K  E  S  N  T  E  S  G  K  E  E  N  T  -209

TAGAGCAACCTAATAAAGTAAAAGAAGATTCAACAACAAGTCAGCCGTCTGGCTATACAA-720
 I  E  Q  P  N  K  V  K  E  D  S  T  T  S  Q  P  S  G  Y  T  -229

ATATAGATGAAAAAATTTCAAATCAAGATGAGTTATTAAATTTACCAATAAATGAATATG-780
 N  I  D  E  K  I  S  N  Q  D  E  L  L  N  L  P  I  N  E  Y  -249
```

Fig. 6B

```
AAAATAAGGCTAGACCATTATCTACAACATCTGCCCAACCATCGATTAAACGTGTAACCG-840
 E  N  K  A  R  P  L  S  T  T  S  A  Q  P  S  I  K  R  V  T  -269

TAAATCAATTAGCGGCGGAACAAGGTTCGAATGTTAACCATTTAATTAAAGTTACTGATC-900
 V  N  Q  L  A  A  E  Q  G  S  N  V  N  H  L  I  K  V  T  D  -289

AAAGTATTACTGAAGGATATGATGATAGTGAAGGTGTTATTAAAGCACATGATGCTGAAA-960
 Q  S  I  T  E  G  Y  D  D  S  E  G  V  I  K  A  H  D  A  E  -309

ACTTAATCTATGATGTAACTTTTGAAGTAGATGATAAGGTGAAATCTGGTGATACGATGA-1020
 N  L  I  Y  D  V  T  F  E  V  D  D  K  V  K  S  G  D  T  M  -329

CAGTGGATATAGATAAGAATACAGTTCCATCAGATTTAACCGATAGCTTTACAATACCAA-1080
 T  V  D  I  D  K  N  T  V  P  S  D  L  T  D  S  F  T  I  P  -349

AAATAAAAGATAATTCTGGAGAAATCATCGCTACAGGTACTTATGATAACAAAAATAAAC-1140
 K  I  K  D  N  S  G  E  I  I  A  T  G  T  Y  D  N  K  N  K  -369

AAATCACCTATACTTTTACAGATTATGTAGATAAGTATGAAAATATTAAAGCACACCTTA-1200
 Q  I  T  Y  T  F  T  D  Y  V  D  K  Y  E  N  I  K  A  H  L  -389

AATTAACGTCATACATTGATAAATCAAAGGTTCCAAATAATAATACCAAGTTAGATGTAG-1260
 K  L  T  S  Y  I  D  K  S  K  V  P  N  N  N  T  K  L  D  V  -409

AATATAAAACGGCCCTTTCATCAGTAAATAAAACAATTACGGTTGAATATCAAAGACCTA-1320
 E  Y  K  T  A  L  S  S  V  N  K  T  I  T  V  E  Y  Q  R  P  -429

ACGAAAATCGGACTGCTAACCTTCAAAGTATGTTTACAAATATAGATACGAAAAATCATA-1380
 N  E  N  R  T  A  N  L  Q  S  M  F  T  N  I  D  T  K  N  H  -449

CAGTTGAGCAAACGATTTATATTAACCCTCTTCGTTATTCAGCCAAGGAAACAAATGTAA-1440
 T  V  E  Q  T  I  Y  I  N  P  L  R  Y  S  A  K  E  T  N  V  -469

ATATTTCAGGGAATGGTGATGAAGGTTCAACAATTATAGACGATAGCACAATAATTAAAG-1500
 N  I  S  G  N  G  D  E  G  S  T  I  I  D  D  S  T  I  I  K  -489

TTTATAAGGTTGGAGATAATCAAAATTTACCAGATAGTAACAGAATTTATGATTACAGTG-1560
 V  Y  K  V  G  D  N  Q  N  L  P  D  S  N  R  I  Y  D  Y  S  -509

AATATGAAGATGTCACAAATGATGATTATGCCCAATTAGGAAATAATAATGATGTGAATA-1620
 E  Y  E  D  V  T  N  D  D  Y  A  Q  L  G  N  N  N  D  V  N  -529

TTAATTTTGGTAATATAGATTCACCATATATTATTAAAGTTATTAGTAAATATGACCCTA-1680
 I  N  F  G  N  I  D  S  P  Y  I  I  K  V  I  S  K  Y  D  P  -549
```

Fig. 6C

```
ATAAGGATGATTACACGACTATACAGCAAACTGTGACAATGCAGACGACTATAAATGAGT-1740
 N  K  D  D  Y  T  T  I  Q  Q  T  V  T  M  Q  T  T  I  N  E  -569

ATACTGGTGAGTTTAGAACAGCATCCTATGATAATACAATTGCTTTCTCTACAAGTTCAG-1800
 Y  T  G  E  F  R  T  A  S  Y  D  N  T  I  A  F  S  T  S  S  -589

GTCAAGGACAAGGTGACTTGCCTCCTGAAAAAACTTATAAAATCGGAGATTACGTATGGG-1860
 G  Q  G  Q  G  D  L  P  P  E  K  T  Y  K  I  G  D  Y  V  W  -609

AAGATGTAGATAAAGATGGTATTCAAAATACAAATGATAATGAAAAACCGCTTAGTAATG-1920
 E  D  V  D  K  D  G  I  Q  N  T  N  D  N  E  K  P  L  S  N  -629

TATTGGTAACTTTGACGTATCCTGATGGAACTTCAAAATCAGTCAGAACAGATGAAGATG-1980
 V  L  V  T  L  T  Y  P  D  G  T  S  K  S  V  R  T  D  E  D  -649

GGAAATATCAATTTGATGGATTGAAAAACGGATTGACTTATAAAATTACATTCGAAACAC-2040
 G  K  Y  Q  F  D  G  L  K  N  G  L  T  Y  K  I  T  F  E  T  -669

CTGAAGGATATACGCCGACGCTTAAACATTCAGGAACAAATCCTGCACTAGACTCAGAAG-2100
 P  E  G  Y  T  P  T  L  K  H  S  G  T  N  P  A  L  D  S  E  -689

GTAATTCTGTATGGGTAACTATTAATGGACAAGACGATATGACGATTGATAGTGGATTTT-2160
 G  N  S  V  W  V  T  I  N  G  Q  D  D  M  T  I  D  S  G  F  -709

ATCAAACACCTAAATACAGCTTAGGGAACTATGTATGGTATGACACTAATAAAGATGGTA-2220
 Y  Q  T  P  K  Y  S  L  G  N  Y  V  W  Y  D  T  N  K  D  G  -729

TTCAAGGTGATGATGAAAAAGGAATCTCTGGAGTTAAAGTGACGTTAAAAGATGAAAACG-2280
 I  Q  G  D  D  E  K  G  I  S  G  V  K  V  T  L  K  D  E  N  -749

GAAATATCATTAGTACAACTACAACCGATGAAAATGGAAAGTATCAATTTGATAATTTAA-2340
 G  N  I  I  S  T  T  T  D  E  N  G  K  Y  Q  F  D  N  L  -769

ATAGTGGTAATTATATTGTTCATTTTGATAAACCTTCAGGTATGACTCAAACAACAACAG-2400
 N  S  G  N  Y  I  V  H  F  D  K  P  S  G  M  T  Q  T  T  T  -789

ATTCTGGTGATGATGACGAACAGGATGCTGATGGGGAAGAAGTTCATGTAACAATTACTG-2460
 D  S  G  D  D  D  E  Q  D  A  D  G  E  E  V  H  V  T  I  T  -809
                                                        →R
ATCATGATGACTTTAGTATAGATAACGGATACTATGATGACGAATCGGATTCCGATAGTG-2520
 D  H  D  D  F  S  I  D  N  G  Y  Y  D  D  E  S  D  S  D  S  -829

ACTCAGACAGCGACTCAGATTCCGATAGTGATTCAGACTCCGATAGCGACTCGGATTCAG-2580
 D  S  D  S  D  S  D  S  D  S  D  S  D  S  D  S  D  S  D  S  -849
```

Fig. 6D

```
ACAGCGACTCAGATTCAGACAGCGACTCGGATTCTGATAGCGACTCGGATTCAGACAGCG-2640
 D  S  D  S  D  S  D  S  D  S  D  S  D  S  D  S  D  S  D  S -869

ACTCAGACTCAGACAGTGATTCAGATTCAGACAGCGACTCAGATTCCGATAGTGATTCAG-2700
 D  S  D  S  D  S  D  S  D  S  D  S  D  S  D  S  D  S  D  S -889

ACTCAGACAGCGACTCAGATTCTGATAGTGATTCAGACTCAGACAGTGATTCAGATTCAG-2760
 D  S  D  S  D  S  D  S  D  S  D  S  D  S  D  S  D  S  D  S -909

ACAGCGACTCAGATTCCGATAGTGATTCAGACTCAGACAGCGACTCAGATTCCGATAGTG-2820
 D  S  D  S  D  S  D  S  D  S  D  S  D  S  D  S  D  S  D  S -929

ATTCAGACTCAGACAGCGACTCAGATTCTGATAGTGATTCAGACTCAGACAGTGATTCAG-2880
 D  S  D  S  D  S  D  S  D  S  D  S  D  S  D  S  D  S  D  S -949

ACTCAGACAGTGATTCAGATTCCGATAGTGATTCAGACTCCGATAGCGACTCAGACTCGG-2940
 D  S  D  S  D  S  D  S  D  S  D  S  D  S  D  S  D  S  D  S -969

ATAGTGACTCAGATTCTGATAGTGATTCAGACTCCGATAGCGACTCAGACTCGGATAGTG-3000
 D  S  D  S  D  S  D  S  D  S  D  S  D  S  D  S  D  S  D  S -989

ACTCAGATTCTGATAGTGATTCAGACTCAGACAGCGACTCAGATTCTGATAGTGATTCAG-3060
 D  S  D  S  D  S  D  S  D  S  D  S  D  S  D  S  D  S  D  S -1009

ACTCAGTCAGTGATTCAGATTCCGATAGTGATTCAGACTCAGGCAGTGATTCGGATTCCG-3120
 D  S  V  S  D  S  D  S  D  S  D  S  D  S  G  S  D  S  D  S -1029

R←
ATAGTGATTCAGACTCAGACAACGACTCAGATTTAGGCAATAGCTCAGATAAGAGTACAA-3180
 D  S  D  S  D  S  D  N  D  S  D  L  G  N  S  S  D  K  S  T -1049

→M
AAGATAAATTACCTGATACAGGAGCTAATGAAGATTATGGCTCTAAAGGCACGTTACTTG-3240
 K  D  K  L  P  D  T  G  A  N  E  D  Y  G  S  K  G  T  L  L -1069

GAACTCTGTTTGCAGGTTTAGGAGCGTTATTATTAGGGAAACGTCGCAAAAATAGAAAAA-3300
 G  T  L  F  A  G  L  G  A  L  L  L  G  K  R  R  K  N  R  K -1089

ATAAAAATTAAAATGTTCAAATGAAATTTGTAGAAAGAAGCAGATATGAGATTTGAATAG-3360
 N  K  N  *                                                 -1092

AAAGTAGATTTAGTCCAACAAATGTAAGATGTTGATTAAAACTATAATATAACTTTCACG-3420
```

Fig. 6E

TTTATCATATCTTGTGAAAAAGATGATGCAAACAAGGTCATTTCTATTAAAAATGACTTA-3480

AATGTATGATTTTTAGAGAAACATATACAACTCACAATCTGACAATGATTTAATAGAGGA-3540

ACCGTGAATTTTAAATGAATTCATGGTTCCTTTTTATTGAATTAATAAAAATTCTTTTAT-3600

—□— Preimm No 1
—◇— Preimm No 2
—○— Serum against GST- FIG
—△— Serum against FIG

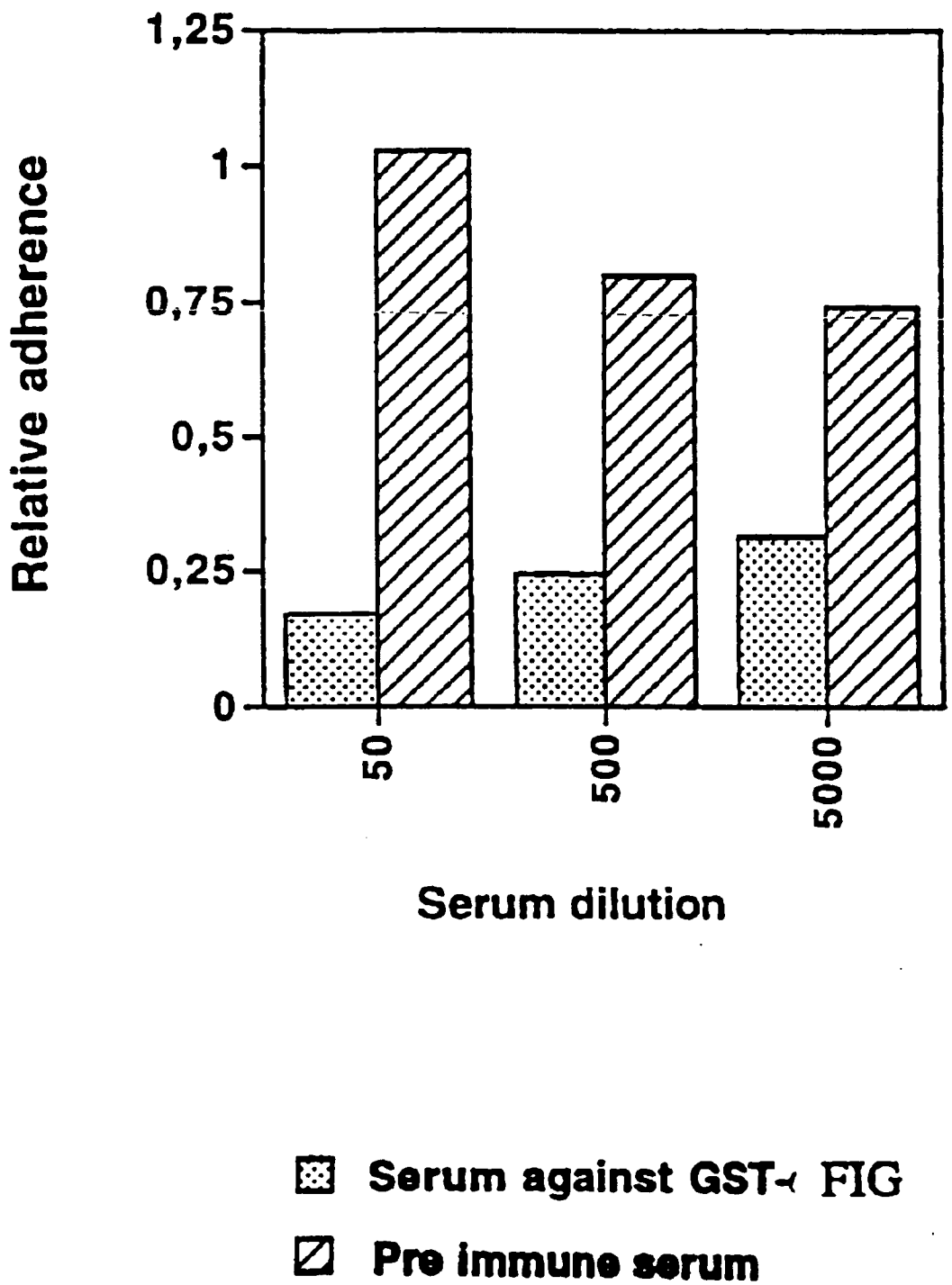

FIBRINOGEN BINDING PROTEIN ORIGINATING FROM COAGULASE-NEGATIVE STAPHYLOCOCCUS

The invention relates to the field of gene technology and is concerned with recombinant DNA molecules, which contain a nucleotide sequence coding for a protein or polypeptide having fibrinogen-binding activity. Moreover the invention comprises micro-organisms (including viruses) containing the aforesaid molecules, and the use thereof in the production of the aforesaid protein or polypeptide and their use in biotechnology. Further, the present invention comprises diagnostic and therapeutic uses of said new protein, e.g. compositions for active and/or passive immunisation.

BACKGROUND OF THE INVENTION

During the last decade, the coagulase-negative staphylococci (CNS) have attracted an increasing attention. Along with the development of human and veterinary medicine, the number of susceptible hosts have increased. Advanced surgery, an increased use of bio-materials, medication with cytostatics, antibiotics and other drugs together with an increased frequency of antibiotica resistant strains of CNS have increased the susceptibility of the host. Concerning the veterinary importance of the CNS it is known that they can cause e.g. both sub-clinical and clinical inflammation in the bovine udder. The existence of bacteria that bind specifically to fibrinogen has been known for many years. The role of fibrinogen binding in the interaction process between the host and *Staphylococcus aureus* is still not clear but the fibrinogen-binding has been considered as one potential virulence factor of this species for instance in endocarditis (Moreillon et al 1995). No protein with fibrinogen binding properties has hitherto been described originating from CNS. However, the present invention describes the characterization and isolation of such protein using gene cloning. Furthermore, the invention describes different methods to measure the fibrinogen binding activity on cells of CNS and the use of this protein in biotechnology.

Generally, it might be difficult to obtain a homogeneous and a reproducible product if such a binding protein was prepared from staphylococcal cells directly. Moreover staphylococci are pathogenic and need complex culture media, which involves complications in large-scale cultures. There is thus a need for a new method for producing a fibrinogen binding protein (or fragments thereof).

SUMMARY OF THE INVENTION

The present invention discloses a new fibrinogen binding protein called FIG, a DNA molecule encoding said protein and applications for their use, according to the attached claims. Importantly, the present invention fills the long felt need of providing methods and means for diagnosing, type-determination, treatment and prevention of infections, caused by coagulase negative bacteria.

SHORT DESCRIPTION OF THE FIGURES

Figure 2:
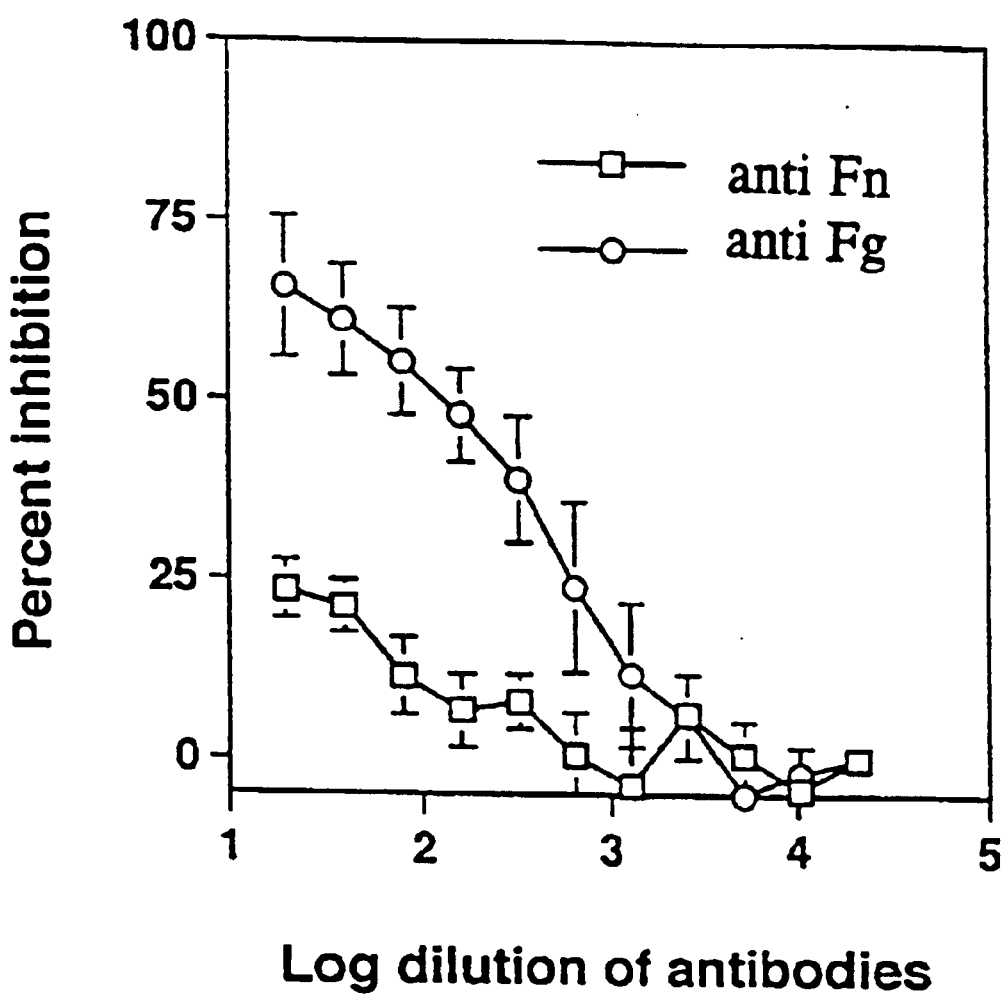
Figure 3:
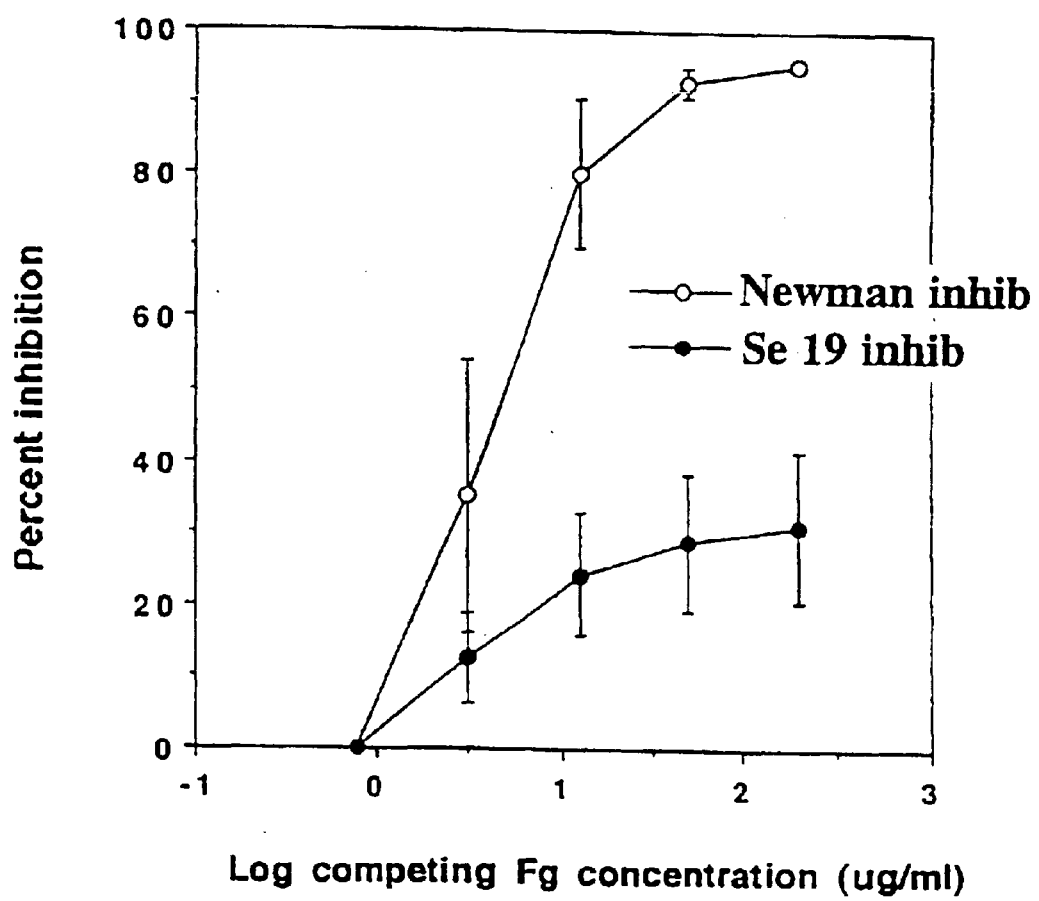
Figure 4:
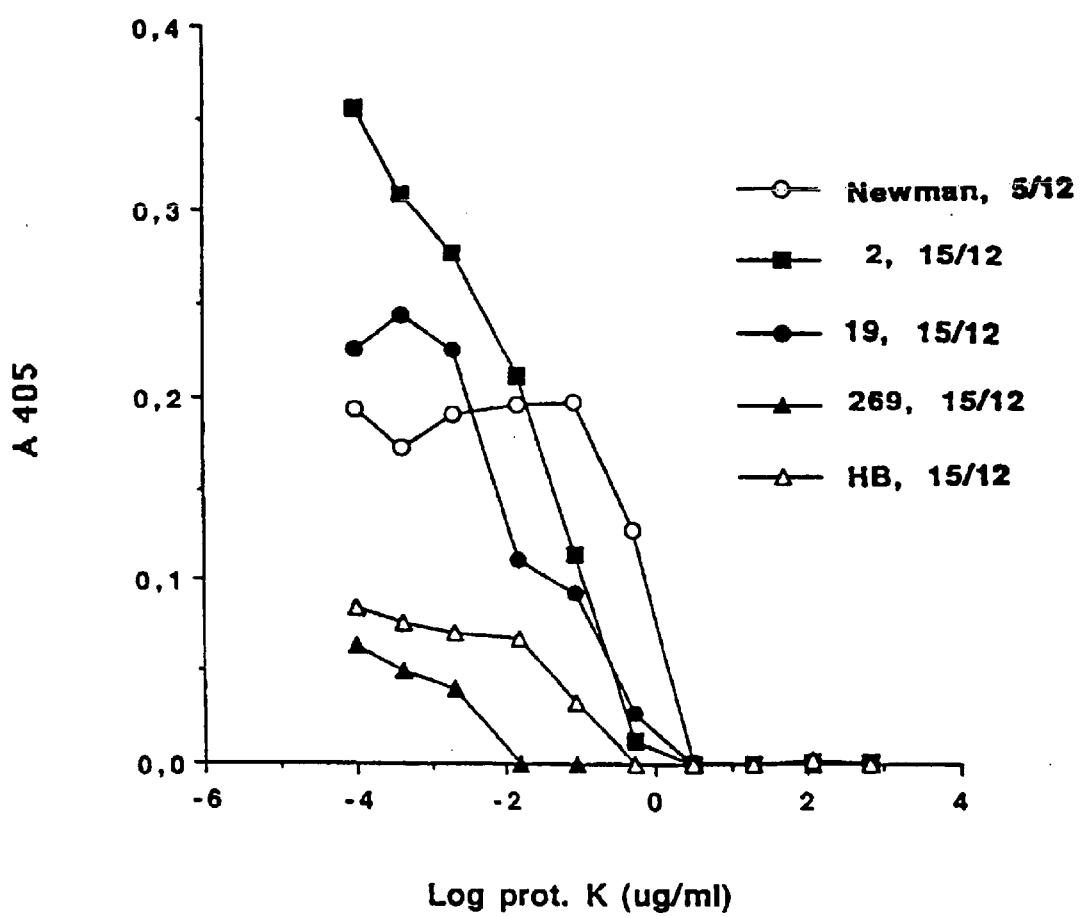
Figure 5:
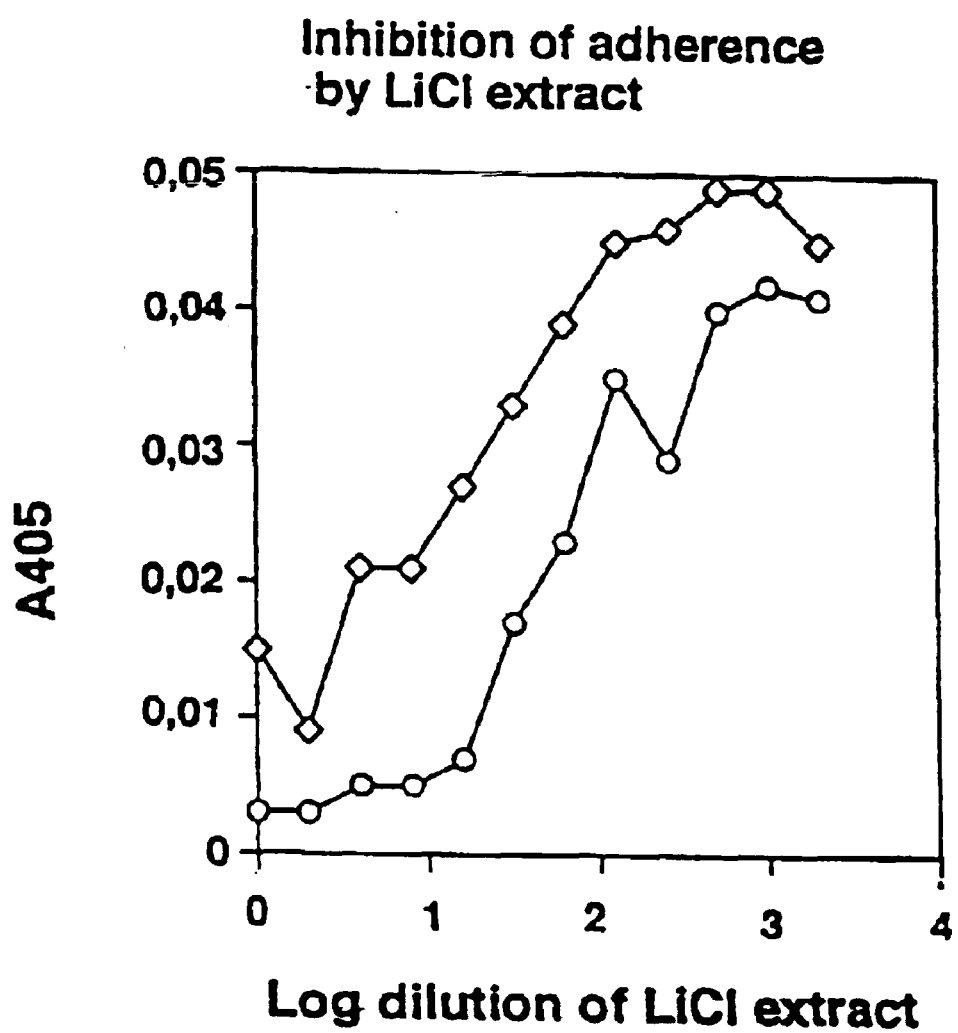

The invention will be described in closer detail in the following, with support of the enclosed examples and figures, in which FIG. 1 shows the adherence values as a function of fibrinogen coating concentration for the *S. epidermidis* strains 2, 19 and JW27 (Example 1A), FIG. 2 shows percent inhibition for antibodies against fibrinogen, compared to antibodies against fibronectin (Example 1B), FIG. 3 shows percent inhibition as a function of competing fibrinogen concentration (Example 1C), FIG. 4 shows the protease sensitivity of adherence to fibrinogen (Example 1D), FIG. 5 shows the inhibition of adherence by LiCl extract (Example 1E), FIGS. 6A–6E show the complete nucleotide sequence of the fig gene from *S. epidermidis* strain HB and the deduced amino acid sequence of the encoded protein (SEQ ID NO:14). A putative ribosomal binding site (RBS) is underlined and a possible transcription termination hairpin loop is double underlined. A putative signal sequence (S) is indicated with an arrow and the translational stop codon with an asterix. The start of the non-repetitive N-terminal region called A, harbouring the fibrinogen binding activity is indicated by an arrow. R indicates the highly repetitive region. The 5 amino acid motif involved in cell wall anchoring is indicated in bold characters and the membrane-spanning region is marked M (Example 3 ).

Figure 7:
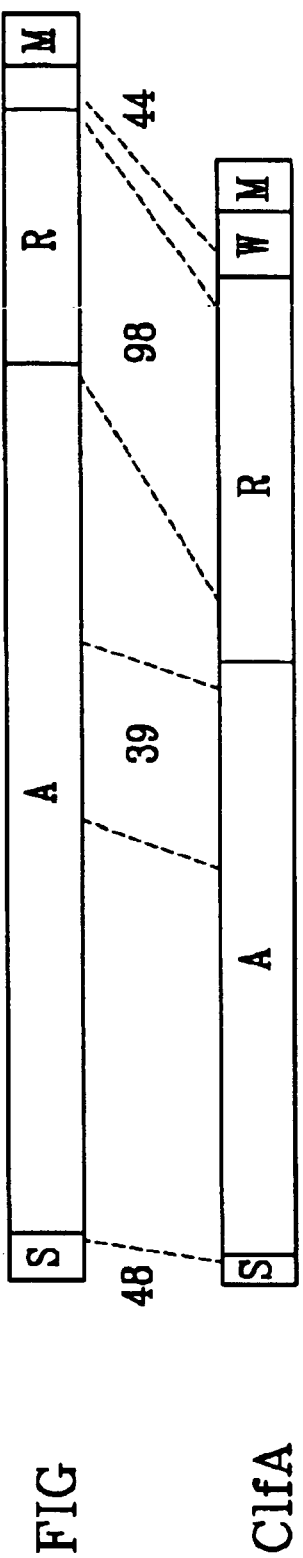
Figure 8:
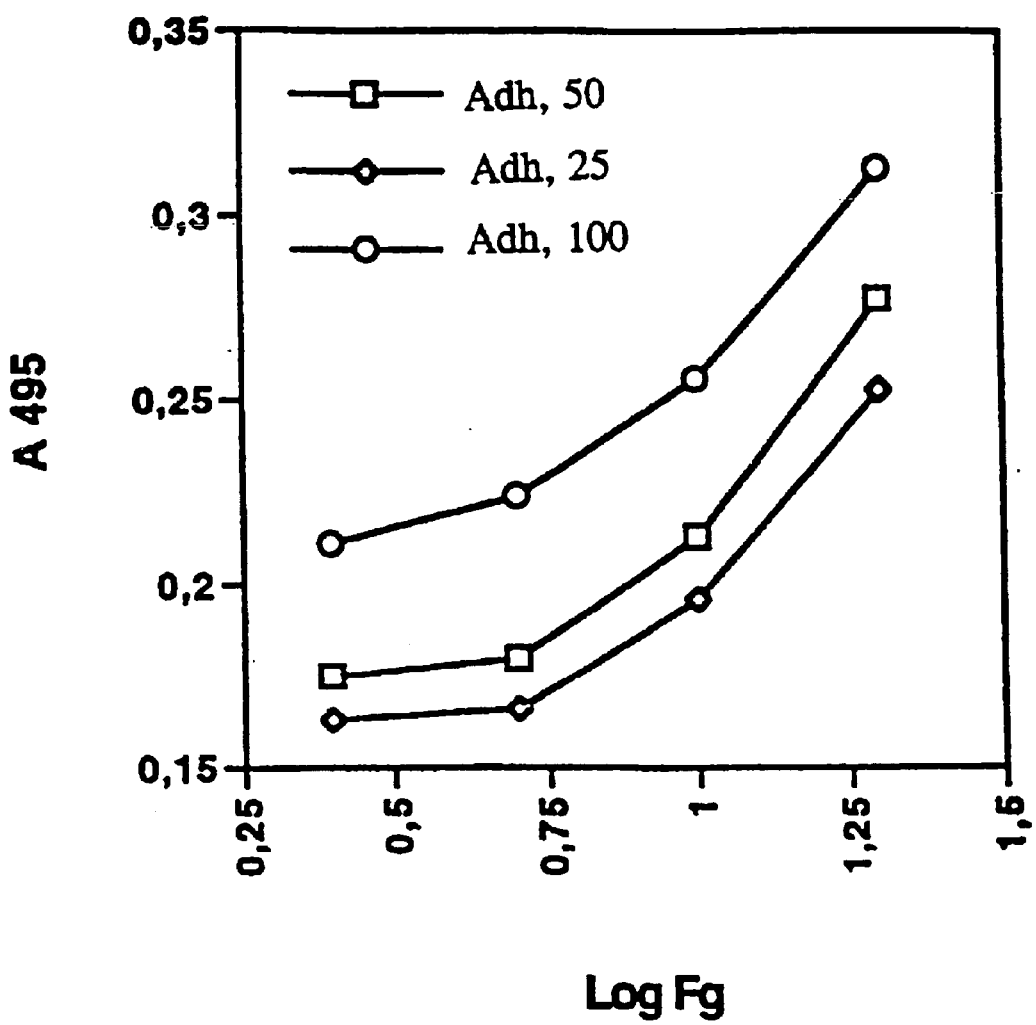
Figure 9:
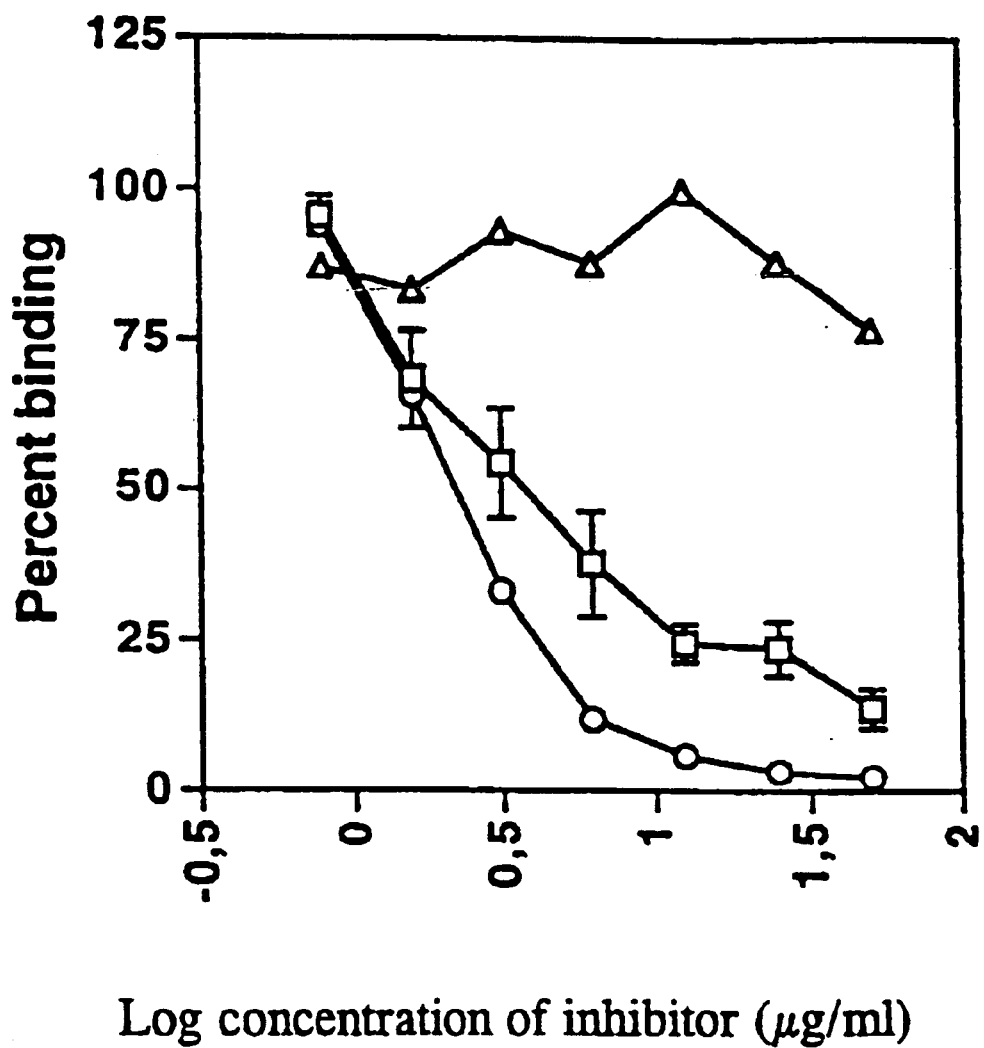
Figure 10:
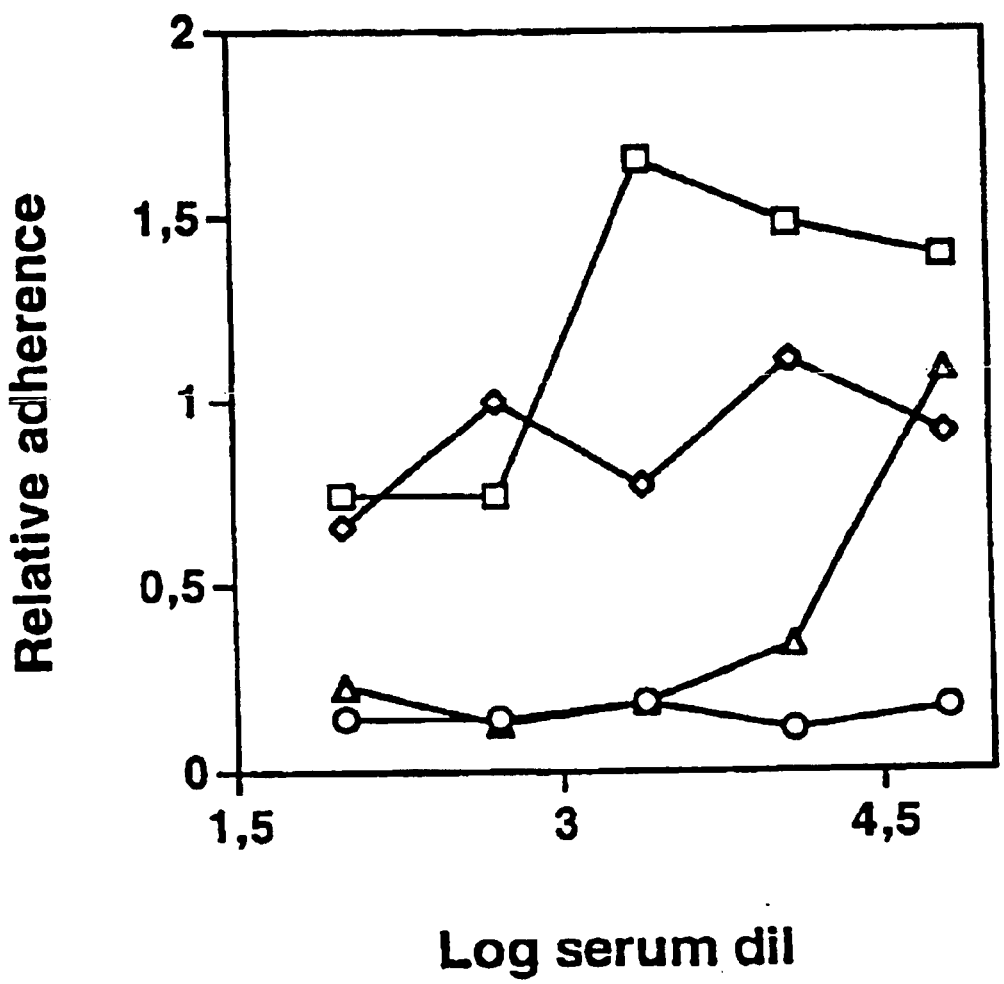

FIG. 7 shows a schematic drawing comparing the fibrinogen binding protein FIG of *S. epidermis* and the clumping factor (ClfA) of *S. aureus*. The similarity, (%), of corresponding regions in the proteins is indicated in the figure between the two protein bars. S is the signal sequence; A, the non-repetitive region harbouring the fibrinogen binding activity, R, the diamino acid residue repeat region; W the region proposed to be involved in cell wall anchoring and M, the transmembrane domain. The numbers indicated refer to the amino acid positions in respective proteins as shown in FIGS. 6A–6E and 7 and in reference (McDevitt et al., 1994) (Example 3), FIG. 8 shows how GST-FIG fusion protein is captured to fibrinogen in a dose dependent way (Example 10), FIG. 9 shows the decrease of bacterial binding as a function of GST-FIG fusion protein, GST or FIG (Example 11), FIG. 10 shows the relative adherence as function of serum dilution for two pre immune sera and a serum against GST-FIG and FIG, respectively (Example 12) and FIG. 11 shows the relative bacterial adherence as a function of serum dilution for, on one hand, pre immune serum and, on the other hand, serum against GST-FIG (Example 12).

DESCRIPTION OF THE INVENTION

The present invention relates to a recombinant DNA molecule comprising a nucleotide sequence, which codes for a protein or polypeptide having fibrinogen-binding activity. The natural source of this nucleotide sequence is of course the *S. epidermidis* strain HB but with the knowledge of the nucleotide and deduced amino acid sequence presented here, the gene or parts of the gene can be isolated or made synthetically. In particular the knowledge of the deduced amino acid sequence for the part of the protein responsible for the fibrinogen binding activity can be used to produce synthetic polypides, which retain or inhibit the fibrinogen binding. These polypeptides can be labelled with various compounds such as enzymes, fluorescence, biotin (or derivatives of), radioactivity, etc. and used e.g. in diagnostic tests such as ELISA- or RIA-techniques.

For production of a recombinant DNA molecule according to the invention a suitable cloning vehicle or vector, for example a phagemid, plasmid or phage DNA, may be cleaved with the aid of a restriction enzyme whereupon the DNA sequence coding for the desired protein or polypeptide is inserted into the cleavage site to form the recombinant DNA molecule. This general procedure is well known to a skilled person, and various techniques for cleaving and ligating DNA sequences have been described in the literature (see for instance U.S. Pat. No. 4,237,224; Ausubel et al 1991; Sambrook et al 1989). Nevertheless, to the present inventors' knowledge, these techniques have not been used for the present purpose. If the S. epidermidis strain HB is used as the source of the desired nucleotide sequence it is possible to isolate said sequence and to introduce it into a suitable vector in manner such as described in the experimental part below or, since the nucleotide sequence is presented here, use a polymerase chain reaction (PCR)-technique to obtain the complete or fragments of the fig gene.

Hosts that may be used are, micro-organisms (which can be made to produce the protein or active fragments thereof), which may comprise bacterial hosts such as strains of e.g. Escherichia coli, Bacillus subtilis, Staphylococcus sp., Lactobacillus sp. and furthermore yeasts and other eukaryotic cells in culture. To obtain maximum expression, regulatory elements such as promoters and ribosome binding sequences may be varied in a manner known per se. The protein or active peptide thereof can be produced intra- or extracellularly. To obtain good secretion in various bacterial systems different signal peptides could be used. To facilitate purification and/or detection the protein or fragment thereof could be fused to an affinity handle and/or enzyme. This can be done on both genetic and protein level. To modify the features of the protein or polypeptide thereof the gene or parts of the gene can be modified using e.g. in vitro mutagenesis; or by fusion of other nucleotide sequences that encode polypeptides resulting in a fusion protein with new features.

The invention thus comprises recombinant DNA molecules containing a nucleotide sequence, which codes for a protein or polypeptide having fibrinogen-binding properties. Furthermore the invention comprises vectors such as e.g. plasmids and phages containing such a nucleotide sequence, and organisms, especially bacteria as e.g. strains of E. coli, B. subtilis and Staphylococcus Sp., into witch such a vector has been introduced. Alternatively, such a nucleotide sequence may be integrated into the natural genome of the micro-organism.

The application furthermore relates to methods for production of a protein or polypeptide having the fibrinogen binding activity of protein FIG or active fragments thereof. According to this method, a micro-organism as set forth above is cultured in a suitable medium, whereupon the resultant product is isolated by some separating method, for example ion exchange chromatography or by means of affinity chromatography with the aid of fibrinogen bound to an insoluble carrier.

Vectors, especially plasmids, which contain the protein FIG encoding nucleotide sequence or parts thereof may advantageously be provided with a readily cleavable restriction site by means of which a nucleotide sequence that codes for another product, can be fused to the protein FIG encoding nucleotide sequence, in order to express a so called fusion protein. The fusion protein may be isolated by a procedure utilising its capacity of binding to fibrinogen, whereupon the other component of the system may if desired be liberated from the fusion protein. This technique has been described at length in WO 84/03103 in respect of the protein A system and is applicable also in the present context in an analogous manner. The fusion strategy may also be used to modify, increase or change the fibrinogen binding activity of protein FIG (or part thereof) by fusion of other fibrinogen binding molecules.

The present invention also applies to the field of biotechnology that concerns the use of bacterial cell surface components as immunogens for vaccination against CNS infections. Immunisation using whole bacteria will always trigger a highly polyclonal immunresponse with a low level of antibodies against a given antigenic determinant. It is therefor preferable to use the protein, polypeptide or DNA according to the present invention for immunisation therapies. Notably, immunisation therapies can be conducted as so called passive and active immunisation. Passive immunisation using the inventive protein or DNA involves the raising of antibodies against the said protein or protein encoded by the administered DNA in a suitable host animal, preferably a mammal e.g. a healthy blood donor or a cow, collecting and administering said antibodies to a patient. One preferred embodiment is passive immunisation of a patient prior to surgery, e.g. operations involving foreign implants in the body. Active immunisation using the inventive protein or DNA involves the administration of the said protein or DNA to a patient, preferably in combination with a pharmaceutically suitable immunostimulating agent. Examples of such agents include, but are not limited to the following: cholera toxin and/or derivatives thereof, heat labile toxins, such as E. coli toxin and similar agents. The composition according to the present invention can further include conventional and pharmaceutically acceptable adjuvants, well known to a person skilled in the art of immunisation therapy. Preferably, in an immunisation therapy using the inventive DNA or fractions thereof, said DNA is preferably administered intramuscularly, whereby said DNA is incorporated in suitable plasmide carriers. An additional gene or genes encoding a suitable immunostimulating agent can preferably be incorporated in the same plasmide.

Said immunisation therapies are not restricted to the above-described routes of administration, but can naturally be adapted to any one of the following routes of administration: oral, nasal, subcutaneous and intramuscular. Especially the oral and nasal methods of administration are potentially very promising, in particular for large-scale immunisations.

EXAMPLES

Sarting Materials

Bacterial Strains, Phages and Cloning Vectors

*Staphylococcus epidermidis* strain HB was obtained from Dr Åsa Ljungh, Lund, Sweden. *E. coli* strain TG1 and son MC1061 were used as bacterial host for construction of the library and production of the phage stocks. The *E. coil* phage R408 (Promega, Madison, Wis., USA) was used as helper phage.

The phagemid vector pG8H6 used is described Jacobsson and Frykberg (1 996).

All strains and plasmid- or phagemid- constructs used in the examples are available at the Department of Microbiology at the Swedish University of Agricultural Sciences, Uppsala, Sweden.

Buffers and Media

*E. coli* was grown on LB (Luria Bertani broth) agar plates or in LB broth (Sambrook et al 1989) at 37° C. In appropriate cases the LB medium was supplemented with glucose to a final conc. of 2%. Ampicillin was in appropriate cases added to the E. coli growth media to a final conc. of 50 µg/ml. Staphylococci were grown at 37° C. on blood agar-plates (containing 5% final conc. bovine blood) or in Tryptone Soya Broth (TSB obtined from Oxoid, Ltd Basingstoke, Hants., England) PBS: 0,05M sodium phosphate pH 7.1, 0.9% NaCl. PBS-T: PBS supplemeted with TWEEN 20 to a final conc. of 0.05%.

Preparation of DNA from Staphylococci and Streptococci

Strains of S. epidermidis or S. aureus were grown overnight in TSB. Next morning the cells were harvested and the chromosomal DNA prepared according to Löfdahl et al (1983). Chromosomal DNA from streptococci has earlier been described in WO 95/07300.

Proteins and Other Reagents

Human fibrinogen was obtained from (IMCO Ltd, Stockholm, Sweden). Human serum albumin (HSA), fibronectin, IgA, lactoferrin and transferrin were obtained from Sigma, St. USA). Bovine serum albumin (fraction V, ria grade) was obtained from USB (cat no.10868). $\alpha_2$macroglobulin ($\alpha_2$M) and collagen type I were obtained from Boehringer, Mannheim, Germany). Vitronectin was obtained from Bional, Tartu, Estonia and human IgG from Kabi, Stockholm, Sweden. Elastin was obtained from ICN Pharmaceuticals Inc. CA, USA and pepsin from KEBO LAB, Stockholm, Sweden.

DNA probes were labelled with $\alpha^{32}$P-ATP by a random-priming method (Multiprime DNA labelling system; Amersham Inc, Amersham, England)

Nitrocellulose (NC) filters (Schleicher & Schull, Dassel, Germany) were used to bind DNA in hybridisation experiments or proteins in Western-blot techniques.

In order to analyse protein samples by native or sodium dodecyl sulphate -polyacrylamid gel electrophoresis (SDS-PAGE) the PHAST-system obtained from Pharmacia LKB Biotechnology, Uppsala, Sweden was used according to the supplier's recommendations.

Oligonucleotides used were synthesised by Pharmacia (Uppsala, Sweden).

Micro Well plates (MaxiSorp, Nunc, Copenhagen, Denmark) were used in the panning experiment. Plasmid DNA was prepared using Wizard Minipreps (Promega) and the sequence of the inserts was determined as described by Jacobsson and Frykberg (1995). The sequences obtained were analysed using the PC-gene program (Intelligenetics, Mountain View, Calif., USA)

Routine Methods

Methods used routinely in molecular biology are not described such as restriction of DNA with endonucleases, ligation of DNA fragments, plasmid purification etc since these methods can be found in commonly used manuals (Sambrook et al., 1989, Ausubel et al, 1991). Ligation reactions were performed using Ready-To-Go T4 DNA Ligase (Pharmacia , Uppsala, Sweden). For polymerase chain reaction amplification the Gene Amp™ kit, obtained from Perkin Elmer Cetus, was used. Sequence reactions were performed using "Sequenase, version 2.0" kit (United States Biochemical Corporation, Cleveland, Ohio, USA). Alternatively the ABI PRISM Dye Terminator Cycle Sequencing Ready Reaction Kit was used and the samples analysed using the Applied Biosystems 373A DNA Sequencer.

Example 1

The Adherence of Staphylococcus epidermidis to Immobilised Fibrinogen and Investigation of the Nature of the Binding Mechanism (A–E)

Strains of Staphylococcus epidermidis isolated from cases of peritonitis were grown on Blood agar plates at 37° C. overnight. The bacteria from one plate was harvested with 5 ml phosphate buffered saline (PBS), washed once, and the optical density (OD) was adjusted to 1.0.

(A) Bacterial Adherence

Fibrinogen was dissolved in PBS at 10 mg/ml and added in serial 3-fold dilution to microtiter wells (Nunc), from top to bottom. The plates were incubated overnight at room temperature (RT). To cover uncoated plastic sites the plates were coated with 2 % bovine serum albumin for 1 hour at 37° C. The plates were washed with PBS with 0.05 % TWEEN 20 (PBST). Next, bacteria were added in serial 2-fold dilution in PBST, from left to right, to the fibrinogen coated microtiter plates. Bacterial adherence was allowed for 2 hours at 37° C. or at 4° C overnight. Non-adherent bacteria were washed off and the bound bacteria were air-dried. The crosswise dilution of both fibrinogen and bacteria allows estimation of bacterial binding both as a function of fibrinogen concentration and of amount of bacteria. Determination of bacterial adherence was done by optical reading using a microtiter plate reader at A 405. The turbidity and light scatter caused by bound bacteria results in a reading ranging from 0.00 to 0.20. An example of adherence values as a function of fibrinogen coating concentration is shown in FIG. 1 for three different strains (2, 19 and JW27). These conditions for adherence determination were used in the following experiments.

(s) Adherence Blocking by Antibodies Against Fibrinogen

In a modification of the experiment performed above, antibodies against fibrinogen (anti Fg) (Sigma) were added 1 hour prior to addition of bacteria (OD=1.0) to the immobilised fibrinogen. As a control, antibodies against fibronectin (anti Fn) (Sigma) were added in a separate experiment. FIG. 2 shows that antibodies against fibrinogen (circles) inhibited adherence better than antibodies against fibronectin could (squares). The mean values and standard errors from three separate experiments are shown.

(C) Adherence Blocking by Soluble fibrinogen

Soluble fibrinogen was added to the bacteria at concentrations indicated in FIG. 3 and incubated for 1 hour at 37° C. before addition to plates coated with fibrinogen as described above. Adherence of S. epidermidis strain 19 (filled circles) was inhibited to around 30%. As a control, inhibition of Staphylococcus aureus stain Newman was measured in a similar experimental set-up (open circles). Mean values and standard errors from three separate experiments are shown. Although significant inhibition of adherence of S. epidermidis was obtained, inhibition of S. aureus was more pronounced.

(D) Reduction of Binding After Protease Treatment of Bacteria

Bacteria were treated for 30 minutes at 37° C. with protease K, at concentrations indicated in FIG. 4, prior to addition to immobilised fibrinogen. Protease treated bacteria were extensively washed after protease treatment to avoid protease digestion of the immobilised fibrinogen. Four different strains of S. epidermidis (2, 19, 269 and HB) and S. aureus (strain Newman) were used in this experiment. All strains tested showed sensitivity to protease treatment; thus the adherence to fibrinogen depends on a surface protein.

(E) Adherence blocking by Licl extract of S. epidermidis

S. epidermidis cells, grown and harvested as described above, were treated with 1M LiCl at 40° C. for 2 hours with continuous gentle stirring. The bacteria were centrifuged and the bacteria-free supernatant was filtered and dialysed PBS. Surface associated proteins bound to the cells by hydrphobic interactions are thereby released. This Licl extract, presumably containing a fibrinogen binding protein, was used to inhibit adherence of S. epidermidis to immobilised fibrinogen in the following way: LiCl extract at various dilutions was added to the immobilised fibrinogen and incubated for 1 hour at 37° C. The plates were washed and bacteria added for adhesion testing. FIG. 5 shows that adherence was better the more the LiCl extract was diluted; i.e. an adhesion-inhibitory compound is present in the LiCl extract. Two independent experiments are shown.

Example 2

Isolation of a Clone Expressing Fibrinogen Binding Activity

A gene library of S. epidermidis strain HB was produced in a manner as described by Jacobsson and Frykberg (1996). Staphylococcal DNA was randomly fragmented by sonication. The library resulted in $4 \times 10^7$ independent clones, which after amplification had a titer of $2 \times 10^{10}$ cfu/ml. Two hundred microlitres of the library were added to each of three fibrinogen coated wells and incubated for 4 hour at room temperature (RT). The wells were washed extensively with PBS-T and once with 50 mM Na-citrate/140 mM NaCl, pH 5.4. Finally, the bound phages were eluted stepwise in the same buffer with decreasing pH (3.4 and 1.8). The eluates from the three wells were neutralised with 2 M Tris-HCl, pH 8.6. Aliquots of the eluates were used to infect E. coli TG1 cells, which therafter were grown overnight on LA plates containing glucose and ampicillin. The colonies (obtained after infection of TG1 cells with the phage and eluted at pH 3.4 and 1.8 in the primary panning) were collected by resuspension in LB medium and infected with helper phage R408 [$10^{10}$ plaque-forming units (pfu)] for production of enriched phage stocks. Thereafter, the infected bacteria were mixed with 4 ml 0.5% soft agar and poured on one LA plate with ampicillin. After incubation over night 37° C. the phages were collected as described by Jacobsson and Frykberg (1996). The resulting phage stock was repanned against fibrinogen as described above. The result presented in Table 1, shows that there is an enrichment of clones having affinity to fibrinogen.

TABLE 1

| Panning | Ligand Fibrinogen | IgG |
|---|---|---|
| 1st Wash | $1.6 \times 10^3$ cfu/ml | — |
| pH 5.4 | $1.6 \times 10^3$ cfu/ml | — |
| pH 3.4 | $2.1 \times 10^3$ cfu/ml | — |
| pH 1.8 | $7.0 \times 10^3$ cfu/ml | — |
| 2nd Wash | $1.2 \times 10^3$ cfu/ml | $2.2 \times 10^2$ cfu/ml |
| pH 5.4 | $4.4 \times 10^3$ cfu/ml | $6.2 \times 10^2$ cfu/ml |
| pH 3.4 | $4.3 \times 10^4$ cfu/ml | $1.4 \times 10^3$ cfu/ml |
| pH 1.8 | $2.0 \times 10^3$ cfu/ml | $8.0 \times 10^2$ cfu/ml |

Example 3

DNA Sequencing and Sequence Analysis

Eight colonies coming from the second panning (pH 3.4) against fibrinogen described in Example 2 were chosen for further studies. Phagemid DNA from these colonies was prepared and partially sequenced. Seven of the clones seemed to contain the same insert. One of these seven clones called pSE100 was chosen for further studies. Purified phagemid DNA from the clone pSE100 was analysed by restriction mapping which revealed that the phagemid contained an insert of ~1.8 kilo base pair (kb). The nucleotide (nt) sequences of the complete inserts of pSE100 were determined and the nt and deduced amino acid (aa) sequences were analysed using the PC-gene program. This analysis revealed that the insert of pSE100 contains an open reading frame of 1.745 nt (sequence list). Thus the insert encodes a 582 aa protein, termed protein FIG (and the corresponding gene termed fig), with a calculated molecular mass of ~65 kDa (sequence list). Furthermore, the sequence analysis show that the insert of pSE100 is in the correct reading frame with the vector sequences in the 5'-and 3'-ends. This means that the insert gives rise to a fusion with the pel leader and the myc tail (sequence list) and that he native 5'- and 3'-ends of the fig gene is not present in the pSE100 clone.

To obtain the missing 5' and 3' end of the fig gene a Southern blot analysis was performed using chromosomal DNA from strain HB digested with various restriction enzymes. The probe was prepared as follows; two oligonucleotides (5'CAACAACCATCTCACACAAC3' which is SEQ ID NO:1 and 5'CATCAAATTGATATTTCCCATC3' which is SEQ ID NO:2) were used to PCR amplify a ~1.3 kb fragment from the insert of pSE100. The PCR generated fragments were 32P-labeled using random priming. After hybridisation using stringent conditions the NC-filter was washed and subjected to autoradiography. The result showed that the XbaI cleavage gave a single band in size of ~6 kb. The corresponding fragment was subsequently ligated into XbaI digested pUC18 vector. After transformation clones harbouring the ~6kb XbaI-fragment were identified by colony hybridisation using the same probe as in the Southern blot experiment. One such clone, called pSE101 was chosen for further studies. DNA sequence analysis showed that the fig gene consist of an open reading frame of a 3291 nt, encoding a protein, called FIG of 1097 aa with a calculated molecular mass of ~119 kDa (FIGS. 6A–6E). The FIG protein consist of several typical features found among Gram-positive cell surface bound proteins, like, a N-terminal signal sequence and a C-terminal 5 amino acid motif (indicated in bold characters), followed by a stretch of 17 hydrophobic aa ending in a stretch of charged aa (FIG. 6). Following the signal sequence, there is a region, called A of 773 aa. The insert of pSE100 contains the sequence corresponding to residue 75 to 656 of the A region (FIG. 7). The A region is followed by a highly repetitive region of 216 aa composed of tandemly repeated aspartic acid and secine residues, called R (FIGS. 6A–6E and 7). The dipeptid region consist of an 18 bp sequence unit (consensus of GAX TCX GAX TCX GAX AGX which is SEQ ID NO:3) repeated 36 times. The 18 bp sequence is almost maintained perfect throughout the whole R region except for the second unit which is truncated, consisting of only 12 of the 18 bp and the 3' end of the region where the consensus sequence is slightly disrupted (units 32, 34 and 36). The changes in the later units also result in an amino acid exchange which disrupt the DS repeat.

Using the deduced amino acid sequence of protein FIG protein database were screened for sequence similarities. Interestingly, the search showed that the highest score obtained was for the clumping factor (ClfA) of S. aureus (FIG. 7). This protein binds fibrinogen and has been shown to promote aggregation of bacteria in the present of plasma.

Beside similarities in the N- and C-terminal part encoding the signal sequence and the cell membrane spanning domain, respectively the most obvious similarity with the clumping factor is the repetitive R region. In both ClfA and FIG protein, the DS repeat region is encoded by the same 18 bp consensus unit. Comparing the nucleotide sequences of fig and ClfA shows that the R regions have an extensive homology. In addition, protein FIG also shows homology to ClfA in the A region, the non-repetitive fibrinogen binding domain (FIG. 7).

Example 4

Properties of the Fibrinogen Binding Protein Encoded from pSE100

A) Specificity of the Fibrinogen Binding

The phagemid pSE100 was electroporated into competent E. coli TG1 cells. After growth over night on a LA plate (containing ampicillin and glucose) one colony con pSE100 was grown over night and infected with the helper phage R408 for production of an enriched phage stock. The resulting phage stock containing recombinant phages expressing the insert of pSE100 had a titer of $3 \times 10^9$ cfu/ml. The phage stock of pSE100 was used to pan against 13 different proteins coated in microtiter wells and to one uncoated well. To each well containing the respective protein (or to the uncoated well) 200 µl of the phage stock of pSE100 was added. After panning for three hours at RT under gentle agitation the wells were washed extensively, using PBST and a sample of the last wash was collected. The bound phages were eluted with Na-Citrate buffer pH 1.8. The eluted samples were immediately neutralised using 1M Tris-HCl pH 8.6. The eluted phages and the phages from the wash were allowed to separately infect E. coli TG1 cells and after infection, the cells were plated on LA plates containing ampicillin and glucose. The plates were incubated over night at 37° C. and the frequency of colonies was counted. The result of this experiment is presented in Table 2 which shows the fibrinogen binding specificity of the protein expressed by pSE100.

TABLE 2

| Ligand | Wash | Eluate pH 1.8 |
| --- | --- | --- |
| Fibrinogen | $1.1 \times 10^4$ cfu/ml | $1.4 \times 10^7$ cfu/ml |
| $\alpha_2$M | $2.0 \times 10^2$ cfu/ml | $2.0 \times 10^3$ cfu/ml |
| BSA | $<10^2$ cfu/ml | $8.0 \times 10^2$ cfu/ml |
| Collagen type I | $6.0 \times 10^2$ cfu/ml | $1.2 \times 10^3$ cfu/ml |
| Elastin | $8.0 \times 10^2$ cfu/ml | $5.2 \times 10^3$ cfu/ml |
| Fibronectin | $6.0 \times 10^2$ cfu/ml | $2.4 \times 10^4$ cfu/ml |
| HSA | $8.0 \times 10^2$ cfu/ml | $2.2 \times 10^3$ cfu/ml |
| IgA | $6.0 \times 10^2$ cfu/ml | $6.8 \times 10^4$ cfu/ml |
| IgG | $4.0 \times 10^2$ cfu/ml | $4.4 \times 10^3$ cfu/ml |
| Lactoferrin | $6.0 \times 10^2$ cfu/ml | $8.2 \times 10^3$ cfu/ml |
| Pepsin | $1.8 \times 10^2$ cfu/ml | $3.7 \times 10^4$ cfu/ml |
| Transferrin | $2.0 \times 10^2$ cfu/ml | $2.4 \times 10^3$ cfu/ml |
| Vitronectin | $<10^2$ cfu/ml | $2.2 \times 10^3$ cfu/ml |
| Plastic | $2.4 \times 10^3$ cfu/ml | $9.0 \times 10^3$ cfu/ml |

(B) Inhibition Experiment

The pSE100 phage stock was diluted to a titer of ~$5 \times 10^6$ cfu/ml. Of this phage solution samples (180 µJ) were taken and separately incubated for one hour with different concentrations of fibrinogen, BSA or IgG before transferred to fibrinogen coated microtiter wells. After panning for three hours at RT under gentle agitation, the wells were washed extensively using PBST. The bound phages were eluted with Na-Citrate buffer pH 1.8. The eluted samples were immediately neutralised using 1M Tris-HCl pH 8.6. The eluted phages were allowed to infect E. coli TG1 cells and after infection, the cells were plated on LA plates containing ampicillin and glucos. The plates were incubated over night at 37° C. and the frequency of colonies was counted. The result of this experiment is presented Table 3, which shows that the binding to fibrinogen is inhibited by fibrinogen but not with the other tested proteins.

TABLE 3

| Conc. of different ligands (µg/ml) | Soluble ligands Fibrinogen | BSA | IgG |
| --- | --- | --- | --- |
| 0 | $7.6 \times 10^4$ cfu/ml | $7.6 \times 10^4$ cfu/ml | $7.6 \times 10^4$ cfu/ml |
| 0.1 | $4.4 \times 10^4$ cfu/ml | $7.0 \times 10^4$ cfu/ml | $6.2 \times 10^4$ cfu/ml |
| 1 | $3.6 \times 10^4$ cfu/ml | $9.3 \times 10^4$ cfu/ml | $9.0 \times 10^4$ cfu/ml |
| 10 | $1.5 \times 10^4$ cfu/ml | $6.3 \times 10^4$ cfu/ml | $7.8 \times 10^4$ cfu/ml |
| 100 | $3.8 \times 10^3$ cfu/ml | $6.4 \times 10^4$ cfu/ml | $7.3 \times 10^4$ cfu/ml |
| 1000 | $3.0 \times 10^2$ cfu/ml | $6.9 \times 10^4$ cfu/ml | $7.6 \times 10^4$ cfu/ml |

Example 5

Western Blot Experiment

E. coli cells of strain TG1 and MC1061 containing pSE100 were grown in LB (containing ampicillin and glucose) over night at 37° C. The next morning the cells were harvested by centrifugation, resuspended in LB (containing ampicillin, glucose and 0.1 M IPTG and further incubated at 37° C. Twelve hours later the cells were harvested by centrifugation and both the cells and the supernatant were taken care of. Four volumes of acetone were added to the supernatant and the resulting precipitate was collected by centrifugation, air-dried and resuspended in ice-cold PBS. Prior to electrophoresis the cells and the precipitate from the supernatant were resuspended separately in a sample buffer containing 2.5 % SDS and 5% beta-mercaptoethanol and boiled for two minutes. After denaturation the samples were analysed run under reducing conditions using the PHAST-system (Pharmacia) on a 8–25% gradient gel using SDS-buffer strips. After the electrophoresis was completed a NC-filter previously soaked in PBS was put on the gel and the temperature raised to 45° C. After ~45 minutes the NC-filter was wetted with 1 ml PBS, gently removed and placed in 15 ml PBS containing 0.1 % TWEEN 20 solution (PBST 0.1 %) for 30 minutes in RT (under gentle agitation and with two changes of PBST 0.1% solution). After the last change of PBST 0.1 % fibrinogen was added to a final conc. of 20 ng/ml and the filter was incubated for four hours at RT under gentle agitation. The filter was subsequently washed for 3×10 minutes using PBST 0.1% and HRP-conjugated rabbit anti-human fibrinogen antibodies (DAKO code A 080, diluted 1:500 in PBST 0.1 %) were added and the filter was incubated for I hour at RT under gentle agitation. After washing the filter 3×10 minutes using PBST 0.1 % the bound fibrinogen was visualised by transferring the filter to a solution containing a substrate for the horse radish peroxidase (6 ml 4-chloro-1-naphtol (3 mg/ml in methanol)+25 ml PBS+20 µl $H_2O_2$). The result showed that a fibrinogen binding protein was found in both types of samples (cells and growth media) in both E. coli cells harbouring pSE100, while no such protein was found in the control cultures of E. coli TG1 and MC1061. The fibrinogen binding protein expressed from the pSE100 was in the approximate size as expected from the deduced amino acid.

Example 6

The Occurrence of the fig Gene and the Use of fig Gene to Identify S. epidermidis in Diagnostic Test Purified chromosomal DNA from S. aureus strain 8325-4, Streptococcus equi subsp. equi strain 196 and subspecies zooepidemicus strain Z5, Streptococcus pyogenes strain 2-1047, Streptococcus dysgalactiae strain 8215 were cleaved using the restriction enzyme EcoRI. The cleaved samples were run on an 0.8% agaros-gel together with chromosomal DNA from S. epidermidis strain HB cleaved with various restriction enzymes. After the electrophoresis was completed, the seperated DNA fragments were transferred to a NC-filter using the Vacuum blotting system from Pharmacia. After the transfer the filter was hybridised under stringent conditions (in a solution containing 6×SSC, 5×Denhart, 0.5% SDS at 65° C.) using a probe designed based on the nucleotide sequence of the insert of pSE100. This probe had earlier been prepared as follows, two oligonucleotides: (5'-AGGTCAAGGACAAGGTGAC-3' which is SEQ ID NO: 4 and 5'-CAACAACCATCTCAC ACAAC-3) which is SEQ ID NO: 1 were ordered (Pharmacia) and used as a primer pair in a PCR (25 cycles of 94° C. 1 minute, 50° C. 30 seconds, 72° C. 1 minute using an Perkin Elmer Cetus Thermal Cycler 480) to amplify an ~150 bp fragment of the insert of pSE100. The amplified material was run on an agarose gel and the ~150 bp fragment was purified and radioactively labelled using $^{32}$p-dATP and the Multiprime DNA labelling system (Amersham). The filter was hybridised over night and subsequently washed in a washing solution (0.2% SSC, 0.1% SDS) at 60° C. and autoradiographed. The result showed that no hybridisation was detected in the samples originating from streptococci and S. aureus while hybridisation occured to the samples coming from the S. epidermidis stain HB.

To investigate the occurrence of the fig gene in other strains of S. epidermidis the following PCR reaction was set up. Chromosomal DNA from 13 different clinical isolates of S. epidermidis was used as templates. The same primers and the same PCR conditions as described above were used. The result showed that an amplified product of ~150 bp could be detected (using a 2% agarose gel) in all strains of S. epidermidis but not in the control samples original containing chromosomal DNA from S. aureus and S. pyogenes.

Example 7

A PCR Amplification Assay for Analysis of Corresponding DS Repeat Regions from Various Isolates of S. epidermidis McDevitt and Foster (Microbiology, 1995,141:937–943) have shown that the DS repeat region in various isolates of S. aureus strains may differ considerable. To investigate if the DS repeat region in S. epidermidis also varies in size between different isolates follow experiment was performed. A pair of primers (5'CCGATGAAAATGGAAAGTATC3' which is SEQ ID NO: 5 and 5'TCCGTTATCTATACTAAAGTC3') which is SEQ ID NO: 6 hybridising on the 5' and 3' side, respectively, of the DS repeat region of protein FIG were used to PCR amplify the corresponding region in 11 different isolates of S. epidermidis. The amplification was performed as follows, after initial denaturation for 1 min. at 95° C. a cycle started with a denaturation step for 30 sec. at 95° C., followed by an annealing time of 1 min. at 50° C. and a elongation period of 2 min. at 72° C. The cycle was repeated 25 times and ended in an final elongation period of 7 min. at 72° C. The PCR products a the DS region of respective strain were analysed by agarose-gel electrophoresis. The result showed that one band of various length was present in each sample. The conclusion from this is that this type of method can be used as a diagnostic test to get a "fingerprint" of a particular strain. This might be useful in e.g. tracing the origin of an infection.

Example 8

The Use of the DS Fragment of Strain HB to Identify Other Homologous Genes in Coagulase-positive and -Negative Staphylococci A DNA fragment consisting of the DS repeat region was constructed as follows. One pair of oligonucleotide primers (5'ACTGATCATGATGACTTAGT 3' which is SEQ ID NO: 7 and 5'TCCGTTATCTAT ACTAAAGTC3') which is SEQ ID NO: 6 was used to PCR amplify the DS region of strain HB using the same conditions as described above. The amplification resulted in a ~700 bp fragment which was radioactively ($^{32}$P) labelled using random priming. This probe was used in a Southern blot analysis using chromosomal DNA (cleaved with EcoRI) from various species of staphylococci (S. aureus, S. epidermidis strain HB, S. haemolyticus strain 789 and strain SM131, S. lugdunensis, S. schleiferi, S. intermedius, S. lentus, S. sciuri, S. carnosus, S. saprophyticus and S. hyicus.

The hybridisation was performed under stringent conditions at 65° C. over night. The need day the filter was washed at 65° C., using 2×SSC following autoradiography. The result showed that at least one specific band was present for the following species; S. aureus, S. epidermidis strain HB, S. haemolyticus strain 789 and strain SM131, S. lugdunensis, S. intermedius, S. sciuri, S. carnosus (weak signal) and S. hyicus. This result shows, that it is possible to clone and identify the corresponding regions in these species.

Example 9

Production of GST-FIG

By polymerase chain reaction, a DNA fragment was amplified encoding a portion of the fibrinogen binding protein. Upper primer was GCGGATCCAATCAGT-CAATAAACACCGACGAT (SEQ ID NO:8) and lower primer was CGGAATTCTGTTCGGACTGATTTG-GAAGTTCC (SEQ ID NO:9). Amplification was done for 30 cycles at 94° C. 30 seconds, 60° C. 30 seconds, 72° C. 2 minutes beginning with 94° C. for 4 minutes and ending with 72° C. for 4 minutes. The amplified fragment was digested with EcoRI and Bam HI. Plasmid pGXT4T (Pharmacia, Uppsala, Sweden) was digested with EcoRI and Bam HI, mixed with the digested fragment and the mixture ligated using T4 DNA ligase according to standard procedures. The ligated DNA was transformed into E. coli strain TG1. A transformant was isolated with a plasmid encoding a fusion protein composed of glutathione thio transferase and fibrinogen binding protein. The protein was purified with the vector plasmid according to Pharmacia's instructions. The purified GST-FIG protein was subjected to Western affinity blot. It was run on polyacrylamide gel electrophoresis, transferred to nitrocellulose paper by passive diffusion, the paper treated with fibrinogen (5 µg/ml) for 2 hours at room temperature, followed by rabbit anti fibrinogen antibodies conjugated to HRP. A band corresponding to a molecular weight of approx. 100 kDa was seen. Omitting fibrinogen in a control experiment displayed no band.

Example 10

Demonstration of Binding of GST-FIG to Stationary Phase Fibrinogen

Microtiter wells were coated with human fibrinogen (Sigma Chemicals Co.) at a concentration ranging from 2.5 to 20 µg/ml at room temperature overnight. The plates were aftercoated with 2% bovine serum albumin (BSA) for one hour at 37° C. The microtiter plates were washed three times and GST-FIG was added to the wells at concentrations of 25, 50 or 100 μg/ml (indicated by the three separate lines in FIG. 8) and the plates incubated for two hours at 37° C. Capture of GST-FIG to the fibrinogen layer was, after washing, detected by antibodies (diluted 1000 times) raised in a rat against His-FIG. Binding of antibodies was, after washing, detected with rabbit anti rat IgG antibodies conjugated with HRP. The substrate for HRP was OPD tablets (Dakopetts) with $H_2O_2$. Colour reaction was measured at 495 nm. FIG. 8 shows that GST-FIG is captured to fibrinogen in a dose dependent way.

Example 11

Inhibition of *S. epidermis* Adherence to Fibrinogen by FIG

Fibrinogen at 2 μg/ml was used to coat microtiter wells overnight at room temperature and aftercoated as above. GST-FIG fusion protein, GST or FIG was added at concentrations indicated in FIG. 9. Radioactively labelled bacteria was added immediately after, and incubated at 37° C. for two hours. Decrease of bacterial binding as a function of GST-FIG fusion protein, GST or FIG is shown in FIG. 9. The symbols in FIG. 9 are the following: squares—inhibition by GST-FIG (mean and SE of five independent experiments are shown); triangles—inhibition by GST carrier protein; circles—inhibition by FIG after thrombin digestion. Only the fusion protein and FIG molecules could inhibit binding.

Radioactive labelling of bacteria was obtained by growing them in the presence of tritiated thymidine (20 μCi/ml specific 81 Ci/mmole) for 5 hours in LB.

Cleavage of GST-FIG was achieved by adding thrombin and incubating at 37° C. for 2 hours.

Example 12

Inhibition of *S. epidermidis* Adherence to Fibrinogen by Antibodies Against GST-FIG and FIG Fibrinogen at 2 mg/ml was used to cost microtiterwells overnight at room temperature and aftercoated as above. Radiolabelled *S. epidermidis* were incubated with different dilutions of sera for 1 hour at 37° C. The bacteria—serum mixtures were then added to the wells and adherence was allowed to take place for two hours at 37° C. Non adherent bacteria were washed away and the amount of adherent bacteria were determined as in example 11 above. Four serum samples were used: 1) Serum from before immunisation from rat No 1. 2) Serum from before immunisation from rat No 2. 3) Serum from rat No 1 immunised with GST-FIG. 4) Serum from rat No 2 immunised with FIG generated by thrombin cleavage. From FIG. 10 it can be seen that adherence is reduced after incubation with sera against FIG or against the GST-FIG fusion protein. With relative adherence of 1.0 is meant the adherence obtained after incubation of the radiolabelled bacteria with phosphate buffered saline.

The experiment was repeated, and data from adherence blocking, using sera taken before immunisation and serum taken after immunisation with GST-FIG is shown in FIG. 11.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

References

Ausubel, F. A., Brent, R, Kingston, R. E., Moore, D. D., Seidman, J. G., Smith, J. A. and Struhl. K. (eds.) (1991) Current Protocols in Molecular Biology, Greene Publishing and Wiley-Intersciences, New York.

Bodén, M. K. and Flock, J.-I. (1995) J.Clin.Microbiol.33: 2347–2352. Incidence of the highly conserved fib gene and expression of the fibrinogen binding (Fib) protein among clinical isolates of *Staphylococcus aureus*.

Jacobsson, K. and Frykberg, L. (1995) Cloning of ligand-binding domains of bacterial receptors by phage display. BioTechniques 18:878–885

Jacobsson, K. and Frykberg L. (1996) Phage display shotgun cloning of ligand-binding domains of prokaryotic receptors approaches 100% correct clones. BioTechniques 20:1070–1081.

Löfdahl, S., Guss, B., Uhlén, M., Philipson, L. and Lindberg, M. (1983) Proc. Natl. Acad. Sci. USA 80:697–701.

McDevitt, D., Francois, P., Vaudaux, P. and Foster, T. J. (1994) Mol. Microbiol. 11:237–248.

Moreillon, P., Entenza, J. M. Francioli, P., McDevitt, D., Foster, T. J.,Francois, P. and Vaudaux, P. (1995) Infect. Immun. 63:4738–4743.

Sambrook, J., Fritsh, E. F. and Maniatis, T.(1989) Molecular cloning, A laboratory manual, second ed, Cold Spring Harbour Labornory Press, New York.

Wadström, T. and Rozgony, F. (1986) Virulence determinants of coagulase-negative staphylococci pp 123–130. In "Coagulase-negative staphylococci" Eds. Mårdh, P.-A. and Schleifer, K. H. Almquist & Wiksell International, Stockholm, Sweden. ISBN 91-22-00783-0. Patents or patent applications cited: WO 95/07300, U.S. Pat. No. 4,237,224, WO 84/03103.

```
Sequence list (SEQ ID NO:10)
          10         20         30         40         50         60         70
           |          |          |          |          |          |          |
      ACCACCACCACCACCACCACCCCTCTAGTGATGAAGAAAAGAATGATGTGATCAATAATAACAGTCAATAA
       H  H  H  H  H  H  P  S  S  D  E  E  K  N  D  V  I  N  N  N  Q  S  I
       <--------------------
          Peg Leader 80         90        100        110        120        130        140
           |          |          |          |          |          |          |
      ACACCGACGATAATAACCAAATAATTAAAAAAGAAGAAACGAATAACTACGATGGCATAGAAAAACGCTCAG
       N  T  D  D  N  N  Q  I  I  K  K  E  E  T  N  N  Y  D  G  I  E  K  R  S
```

-continued

```
         150       160       170       180       190       200       210
          |         |         |         |         |         |         |
AAGATAGAACAGAGTCAACAACAAATGTAGATGAAAACGAAGCAACATTTTTACAAAAGACCCCTCAAGATA
 E  D  R  T  E  S  T  T  N  V  D  E  N  E  A  T  F  L  Q  K  T  P  Q  D 220       230       240       250       260       270       280
          |         |         |         |         |         |         |
ATACTCATCTTACAGAAGAAGAGGTAAAAGAATCCTCATCAGTCGAATCCTCAAATTCATCAATTGATACTG
 N  T  H  L  T  E  E  E  V  K  E  S  S  S  V  E  S  S  N  S  S  I  D  T 290       300       310       320       330       340       350       360
  |         |         |         |         |         |         |         |
CCCAACAACCATCTCACACAACAATAAATAGAAGAATCTGTTCAAACAAGTGATAATGTAGAAGATTCAC
 A  Q  Q  P  S  H  T  T  I  N  R  E  E  S  V  Q  T  S  D  N  V  E  D  S 370       380       390       400       410       420       430
          |         |         |         |         |         |         |
ACGTATCAGATTTTGCTAACTCTAAAATAAAAGAGAGTAACACTGAATCTGGTAAAGAAGAGAATACTATAG
 H  V  S  D  F  A  N  S  K  I  K  E  S  N  T  E  S  G  K  E  E  N  T  I 440       450       460       470       480       490       500
          |         |         |         |         |         |         |
AGCAACCTAATAAAGTAAAAGAAGATTCAACAACAAGTCAGCCGTCTGGCTATACAAATATAGATGAAAAA
 E  Q  P  N  K  V  K  E  D  S  T  T  S  Q  P  S  G  Y  T  N  I  D  E  K 510       520       530       540       550       560       570
          |         |         |         |         |         |         |
TTTCAAATCAAGATGAGTTATTAAATTTACCAATAAATGAATATGAAAATAAGGCTAGACCATTATCTACAA
 I  S  N  Q  D  E  L  L  N  L  P  I  N  E  Y  E  N  K  A  R  P  L  S  T 580       590       600       610       620       630       640
          |         |         |         |         |         |         |
CATCTGCCCAACCATCGATTAAACGTGTAACCGTAAATCAATTAGCGGCGGAACAAGGTTCGAATGTTAACC
 T  S  A  Q  P  S  I  K  R  V  T  V  N  Q  L  A  A  E  Q  G  S  N  V  N 650       660       670       680       690       700       710       720
 |         |         |         |         |         |         |         |
ATTTAATTAAAGTTACTGATCAAAGTATTACTGAAGGATATGATGATAGTGAAGGTGTTATTAAAGCACATG
 H  L  I  K  V  T  D  Q  S  I  T  E  G  Y  D  D  S  E  G  V  I  K  A  H 730       740       750       760       770       780       790
          |         |         |         |         |         |         |
ATGCTGAAAACTTAATCTATGATGTAACTTTTGAAGTAGATGATAAGGTGAAATCTGGTGATACGATGACAG
 D  A  E  N  L  I  Y  D  V  T  F  E  V  D  D  K  V  K  S  G  D  T  M  T 800       810       820       830       840       850       860
          |         |         |         |         |         |         |
TGGATATAGATAAGAATACAGTTCCATCAGATTTAACCGATAGCTTTACAATACCAAAAATAAAAGATAATT
 V  D  I  D  K  N  T  V  P  S  D  L  T  D  S  F  T  I  P  K  I  K  D  N 870       880       890       900       910       920       930
          |         |         |         |         |         |         |
CTGGAGAAATCATCGCTACAGGTACTTATGATAACAAAAATAAACAAATCACCTATACTTTTACAGATTATG
 S  G  E  I  I  A  T  G  T  Y  D  N  K  N  K  Q  I  T  Y  T  F  T  D  Y 940       950       960       970       980       990      1000
          |         |         |         |         |         |         |
TAGATAAGTATGAAAATATTAAAGCACACCTTAAATTAACGTCATACATTGATAAATCAAAGGTTCCAAATA
 V  D  K  Y  E  N  I  K  A  H  L  K  L  T  S  Y  I  D  K  S  K  V  P  N 1010      1020      1030      1040      1050      1060      1070      1080
 |         |         |         |         |         |         |         |
ATAATACCAAGTTAGATGTAGAATATAAAACGGCCCTTTCATCAGTAAATAAAACAATTACGGTTGAATATC
 N  N  T  K  L  D  V  E  Y  K  T  A  L  S  S  V  N  K  T  I  T  V  E  Y 1090      1100      1110      1120      1130      1140      1150
          |         |         |         |         |         |         |
AAAGACCTAACGAAAATCGGACTGCTAACCTTCAAAGTATGTTTACAAATATAGATACGAAAAATCATACAG
 Q  R  P  N  E  N  R  T  A  N  L  Q  S  M  F  T  N  I  D  T  K  N  H  T 1160      1170      1180      1190      1200      1210      1220
          |         |         |         |         |         |         |
TTGAGCAAACGATTTATATTAACCCTCTTCGTTATTCAGCCAAGGAAACAAATGTAAATATTTCAGGGAATG
 V  E  Q  T  I  Y  I  N  P  L  R  Y  S  A  K  E  T  N  V  N  I  S  G  N 1230      1240      1250      1260      1270      1280      1290
          |         |         |         |         |         |         |
GTGATGAAGGTTCAACAATTATAGACGATAGCACAATAATTAAAGTTTATAAGGTTGGAGATAATCAAAATT
 G  D  E  G  S  T  I  I  D  D  S  T  I  I  K  V  Y  K  V  G  D  N  Q  N
```

```
                                    -continued
     1300      1310      1320      1330      1340      1350      1360
      |         |         |         |         |         |         |
     TACCAGATAGTAACAGAATTTATGATTACAGTGAATATGAAGATGTCACAAATGATGATTATGCCCAATTAG
      L  P  D  S  N  R  I  Y  D  Y  S  E  Y  E  D  V  T  N  D  D  Y  A  Q  L 1370      1380      1390      1400      1410      1420      1430      1440
  |         |         |         |         |         |         |         |
 GAAATAATAATGATGTGAATATTAATTTTGGTAATATAGATTCACCATATATTATTAAAGTTATTAGTAAAT
  G  N  N  N  D  V  N  I  N  F  G  N  I  D  S  P  Y  I  I  K  V  I  S  K 1450      1460      1470      1480      1490      1500      1510
            |         |         |         |         |         |         |
     ATGACCCTAATAAGGATGATTACACGACTATACAGCAAACTGTGACAATGCAGACGACTATAAATGAGTATA
      Y  D  P  N  K  D  D  Y  T  T  I  Q  Q  T  V  T  M  Q  T  T  I  N  E  Y 1520      1530      1540      1550      1560      1570      1580
         |         |         |         |         |         |         |
     CTGGTGAGTTTAGAACAGCATCCTATGATAATACAATTGCTTTCTCTACAAGTTCAGGTCAAGGACAAGGTG
      T  G  E  F  R  T  A  S  Y  D  N  T  I  A  F  S  T  S  S  G  Q  G  Q  G 1590      1600      1610      1620      1630      1640      1650
         |         |         |         |         |         |         |
     ACTTGCCTCCTGAAAAAACTTATAAAATGGAGATTACGTATGGGAAGATGTAGATAAAGATGGTATTCAAA
      D  L  P  P  E  K  T  Y  K  I  G  D  Y  V  W  E  D  V  D  K  D  G  I  Q 1660      1670      1680      1690      1700      1710      1720
      |         |         |         |         |         |         |
     ATACAAATGATAATGAAAAACCGCTTAGTAATGTATTGGTAACTTTGACGTATCCTGATGGAACTTCAAAAT
      N  T  N  D  N  E  K  P  L  S  N  V  L  V  T  L  T  Y  P  D  G  T  S  K 1730      1740      1750      1760      1770      1780
  |         |         |         |         |         |
 CAGTCAGAACAGATGAAGATGGGAAATATCAATTTGATGGGGTGCAGGTCGAC
  S  V  R  T  D  E  D  G  K  Y  Q  F  D  G  V  Q  V  D
                                            ---------->
```

Sequence list. A partial nucleotide sequence of the putative fig gene from *S. epidermidis* strain HB and the deduced amino acid sequence. The vector sequences in the junction of the 5'- and 3'-ends are indicated.

The nucleotide sequence shown in the above SEQ ID NO: 10 encodes a protein which contains 593 amino acids. SEQ ID NO: 11 is the amino acid sequence of this protein.

SEQ ID NO: 12 is the nucleotide sequence containing 1746 nitrogenous bases which code for the 582 amino acid FIG protein. As discussed above, the 582 amino acid FIG protein is encoded by the insert of pSE100. The nucleotide sequence of SEQ ID NO: 12 corresponds to bases 255–2000 shown in FIGS. 6A–6E.

SEQ ID NO: 13 is the deduced amino acid sequence encoded by SEQ ID-NO: 12. Thus SEQ ID NO: 13 is the 582 amino acid sequence of the FIG protein and thereby corresponds to amino acids 75–656 of the sequence depicted in FIGS. 6A–6E. In other words SEQ ID NO: 13 is the amino acid sequence of SEQ ID NO: 11 without the Pel leader sequence and the Myc tail.

SEQ ID NO: 15-is the deduced amino acid sequence encoded by SEQ ID NO: 14, i.e., the amino acid sequence shown in FIGS. 6A–6E.

What is claimed is:

1. A purified *Staphylococcus epidermidis* protein having the amino acid sequence of SEQ ID NO: 15, or a purified polypeptide having fibrinogen binding activity and having the amino acid sequence of SEQ ID NO:13.

2. A vaccine composition including the protein or the polypeptide according to claim 1.

3. A method of active immunization comprising the administration of the protein according to claim 1 to a mammal.

4. A fusion protein comprising the protein or the polypeptide according to claim 1.

* * * * *

SEQUENCE LISTING

```
<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 1
caacaaccat ctcacacaac                                              20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 2
```
catcaaattg atatttccca tc                                                    22

<210> SEQ ID NO 3
<211> LENGTH: 18
<212> TYPE: DNA
<213> ORGANISM: Staphylococcus epidermidis
<220> FEATURE:
<221> NAME/KEY: variation
<222> LOCATION: (3)
<223> OTHER INFORMATION: n is c or t
<220> FEATURE:
<221> NAME/KEY: variation
<222> LOCATION: (6)
<223> OTHER INFORMATION: n is c, t, a, or g
<220> FEATURE:
<221> NAME/KEY: variation
<222> LOCATION: (9)
<223> OTHER INFORMATION: n is c or t
<220> FEATURE:
<221> NAME/KEY: variation
<222> LOCATION: (12)
<223> OTHER INFORMATION: n is c, t, a, or g
<220> FEATURE:
<221> NAME/KEY: variation
<222> LOCATION: (15)
<223> OTHER INFORMATION: n is c or t
<220> FEATURE:
<221> NAME/KEY: variation
<222> LOCATION: (18)
<223> OTHER INFORMATION: n is c or t

<400> SEQUENCE: 3
gantcngant cnganagn                                                         18

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 4
aggtcaagga caaggtgac                                                        19

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 5
ccgatgaaaa tggaaagtat c                                                     21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 6
tccgttatct atactaaagt c                                                     21

<210> SEQ ID NO 7
<211> LENGTH: 21
<212> TYPE: DNA
<213> ORGANISM: Artificial Sequence
<220> FEATURE:

-continued

<223> OTHER INFORMATION: Description of Artificial Sequence: primer

<400> SEQUENCE: 7
actgatcatg atgactttag t                                                    21

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 8
gcggatccaa tcagtcaata aacaccgacg at                                        32

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 9
cggaattctg ttcggactga tttggaagtt cc                                        32

<210> SEQ ID NO 10
<211> LENGTH: 1781
<212> TYPE: DNA
<213> ORGANISM: Staphylococcus epidermidis
<220> FEATURE:
<221> NAME/KEY: CDS
<222> LOCATION: (3)..(1781)

<400> SEQUENCE: 10

```
ac cac cac cac cac cac cac ccc tct agt gat gaa gaa aag aat gat             47
   His His His His His His Pro Ser Ser Asp Glu Glu Lys Asn Asp
    1               5                  10                  15 gtg atc aat aat aat cag tca ata aac acc gac gat aat aac caa ata            95
Val Ile Asn Asn Asn Gln Ser Ile Asn Thr Asp Asp Asn Asn Gln Ile
             20                  25                  30 att aaa aaa gaa gaa acg aat aac tac gat ggc ata gaa aaa cgc tca           143
Ile Lys Lys Glu Glu Thr Asn Asn Tyr Asp Gly Ile Glu Lys Arg Ser
         35                  40                  45 gaa gat aga aca gag tca aca aca aat gta gat gaa aac gaa gca aca           191
Glu Asp Arg Thr Glu Ser Thr Thr Asn Val Asp Glu Asn Glu Ala Thr
     50                  55                  60 ttt tta caa aag acc cct caa gat aat act cat ctt aca gaa gaa gag           239
Phe Leu Gln Lys Thr Pro Gln Asp Asn Thr His Leu Thr Glu Glu Glu
 65                  70                  75 gta aaa gaa tcc tca tca gtc gaa tcc tca aat tca tca att gat act           287
Val Lys Glu Ser Ser Ser Val Glu Ser Ser Asn Ser Ser Ile Asp Thr
 80                  85                  90                  95 gcc caa caa cca tct cac aca aca ata aat aga gaa gaa tct gtt caa           335
Ala Gln Gln Pro Ser His Thr Thr Ile Asn Arg Glu Glu Ser Val Gln
                100                 105                 110 aca agt gat aat gta gaa gat tca cac gta tca gat ttt gct aac tct           383
Thr Ser Asp Asn Val Glu Asp Ser His Val Ser Asp Phe Ala Asn Ser
            115                 120                 125 aaa ata aaa gag agt aac act gaa tct ggt aaa gaa gag aat act ata           431
Lys Ile Lys Glu Ser Asn Thr Glu Ser Gly Lys Glu Glu Asn Thr Ile
        130                 135                 140 gag caa cct aat aaa gta aaa gaa gat tca aca aca agt cag ccg tct           479
Glu Gln Pro Asn Lys Val Lys Glu Asp Ser Thr Thr Ser Gln Pro Ser
```

```
                145                 150                 155
ggc tat aca aat ata gat gaa aaa att tca aat caa gat gag tta tta      527
Gly Tyr Thr Asn Ile Asp Glu Lys Ile Ser Asn Gln Asp Glu Leu Leu
160                 165                 170                 175 aat tta cca ata aat gaa tat gaa aat aag gct aga cca tta tct aca      575
Asn Leu Pro Ile Asn Glu Tyr Glu Asn Lys Ala Arg Pro Leu Ser Thr
                180                 185                 190 aca tct gcc caa cca tcg att aaa cgt gta acc gta aat caa tta gcg      623
Thr Ser Ala Gln Pro Ser Ile Lys Arg Val Thr Val Asn Gln Leu Ala
            195                 200                 205 gcg gaa caa ggt tcg aat gtt aac cat tta att aaa gtt act gat caa      671
Ala Glu Gln Gly Ser Asn Val Asn His Leu Ile Lys Val Thr Asp Gln
        210                 215                 220 agt att act gaa gga tat gat gat agt gaa ggt gtt att aaa gca cat      719
Ser Ile Thr Glu Gly Tyr Asp Asp Ser Glu Gly Val Ile Lys Ala His
    225                 230                 235 gat gct gaa aac tta atc tat gat gta act ttt gaa gta gat gat aag      767
Asp Ala Glu Asn Leu Ile Tyr Asp Val Thr Phe Glu Val Asp Asp Lys
240                 245                 250                 255 gtg aaa tct ggt gat acg atg aca gtg gat ata gat aag aat aca gtt      815
Val Lys Ser Gly Asp Thr Met Thr Val Asp Ile Asp Lys Asn Thr Val
                260                 265                 270 cca tca gat tta acc gat agc ttt aca ata cca aaa ata aaa gat aat      863
Pro Ser Asp Leu Thr Asp Ser Phe Thr Ile Pro Lys Ile Lys Asp Asn
            275                 280                 285 tct gga gaa atc atc gct aca ggt act tat gat aac aaa aat aaa caa      911
Ser Gly Glu Ile Ile Ala Thr Gly Thr Tyr Asp Asn Lys Asn Lys Gln
        290                 295                 300 atc acc tat act ttt aca gat tat gta gat aag tat gaa aat att aaa      959
Ile Thr Tyr Thr Phe Thr Asp Tyr Val Asp Lys Tyr Glu Asn Ile Lys
    305                 310                 315 gca cac ctt aaa tta acg tca tac att gat aaa tca aag gtt cca aat     1007
Ala His Leu Lys Leu Thr Ser Tyr Ile Asp Lys Ser Lys Val Pro Asn
320                 325                 330                 335 aat aat acc aag tta gat gta gaa tat aaa acg gcc ctt tca tca gta     1055
Asn Asn Thr Lys Leu Asp Val Glu Tyr Lys Thr Ala Leu Ser Ser Val
                340                 345                 350 aat aaa aca att acg gtt gaa tat caa aga cct aac gaa aat cgg act     1103
Asn Lys Thr Ile Thr Val Glu Tyr Gln Arg Pro Asn Glu Asn Arg Thr
            355                 360                 365 gct aac ctt caa agt atg ttt aca aat ata gat acg aaa aat cat aca     1151
Ala Asn Leu Gln Ser Met Phe Thr Asn Ile Asp Thr Lys Asn His Thr
        370                 375                 380 gtt gag caa acg att tat att aac cct ctt cgt tat tca gcc aag gaa     1199
Val Glu Gln Thr Ile Tyr Ile Asn Pro Leu Arg Tyr Ser Ala Lys Glu
    385                 390                 395 aca aat gta aat att tca ggg aat ggt gat gaa ggt tca aca att ata     1247
Thr Asn Val Asn Ile Ser Gly Asn Gly Asp Glu Gly Ser Thr Ile Ile
400                 405                 410                 415 gac gat agc aca ata att aaa gtt tat aag gtt gga gat aat caa aat     1295
Asp Asp Ser Thr Ile Ile Lys Val Tyr Lys Val Gly Asp Asn Gln Asn
                420                 425                 430 tta cca gat agt aac aga att tat gat tac agt gaa tat gaa gat gtc     1343
Leu Pro Asp Ser Asn Arg Ile Tyr Asp Tyr Ser Glu Tyr Glu Asp Val
            435                 440                 445 aca aat gat gat tat gcc caa tta gga aat aat aat gat gtg aat att     1391
Thr Asn Asp Asp Tyr Ala Gln Leu Gly Asn Asn Asn Asp Val Asn Ile
        450                 455                 460 aat ttt ggt aat ata gat tca cca tat att att aaa gtt att agt aaa     1439
```

```
Asn Phe Gly Asn Ile Asp Ser Pro Tyr Ile Ile Lys Val Ile Ser Lys
    465                 470                 475 tat gac cct aat aag gat gat tac acg act ata cag caa act gtg aca      1487
Tyr Asp Pro Asn Lys Asp Asp Tyr Thr Thr Ile Gln Gln Thr Val Thr
480                 485                 490                 495 atg cag acg act ata aat gag tat act ggt gag ttt aga aca gca tcc      1535
Met Gln Thr Thr Ile Asn Glu Tyr Thr Gly Glu Phe Arg Thr Ala Ser
                500                 505                 510 tat gat aat aca att gct ttc tct aca agt tca ggt caa gga caa ggt      1583
Tyr Asp Asn Thr Ile Ala Phe Ser Thr Ser Ser Gly Gln Gly Gln Gly
            515                 520                 525 gac ttg cct cct gaa aaa act tat aaa atc gga gat tac gta tgg gaa      1631
Asp Leu Pro Pro Glu Lys Thr Tyr Lys Ile Gly Asp Tyr Val Trp Glu
        530                 535                 540 gat gta gat aaa gat ggt att caa aat aca aat gat aat gaa aaa ccg      1679
Asp Val Asp Lys Asp Gly Ile Gln Asn Thr Asn Asp Asn Glu Lys Pro
    545                 550                 555 ctt agt aat gta ttg gta act ttg acg tat cct gat gga act tca aaa      1727
Leu Ser Asn Val Leu Val Thr Leu Thr Tyr Pro Asp Gly Thr Ser Lys
560                 565                 570                 575 tca gtc aga aca gat gaa gat ggg aaa tat caa ttt gat ggg gtg cag      1775
Ser Val Arg Thr Asp Glu Asp Gly Lys Tyr Gln Phe Asp Gly Val Gln
                580                 585                 590 gtc gac                                                               1781
Val Asp <210> SEQ ID NO 11
<211> LENGTH: 593
<212> TYPE: PRT
<213> ORGANISM: Staphylococcus epidermidis

<400> SEQUENCE: 11

His His His His His His Pro Ser Ser Asp Glu Glu Lys Asn Asp Val
  1               5                  10                  15

Ile Asn Asn Gln Ser Ile Asn Thr Asp Asp Asn Asn Gln Ile Ile
             20                  25                  30

Lys Lys Glu Glu Thr Asn Asn Tyr Asp Gly Ile Glu Lys Arg Ser Glu
         35                  40                  45

Asp Arg Thr Glu Ser Thr Thr Asn Val Asp Glu Asn Glu Ala Thr Phe
     50                  55                  60

Leu Gln Lys Thr Pro Gln Asp Asn Thr His Leu Thr Glu Glu Val
 65                  70                  75                  80

Lys Glu Ser Ser Ser Val Glu Ser Ser Asn Ser Ser Ile Asp Thr Ala
                 85                  90                  95

Gln Gln Pro Ser His Thr Thr Ile Asn Arg Glu Glu Ser Val Gln Thr
            100                 105                 110

Ser Asp Asn Val Glu Asp Ser His Val Ser Asp Phe Ala Asn Ser Lys
        115                 120                 125

Ile Lys Glu Ser Asn Thr Glu Ser Gly Lys Glu Glu Asn Thr Ile Glu
    130                 135                 140

Gln Pro Asn Lys Val Lys Glu Asp Ser Thr Thr Ser Gln Pro Ser Gly
145                 150                 155                 160

Tyr Thr Asn Ile Asp Glu Lys Ile Ser Asn Gln Asp Glu Leu Leu Asn
                165                 170                 175

Leu Pro Ile Asn Glu Tyr Glu Asn Lys Ala Arg Pro Leu Ser Thr Thr
            180                 185                 190

Ser Ala Gln Pro Ser Ile Lys Arg Val Thr Val Asn Gln Leu Ala Ala
```

-continued

```
            195                 200                 205
Glu Gln Gly Ser Asn Val Asn His Leu Ile Lys Val Thr Asp Gln Ser
        210                 215                 220
Ile Thr Glu Gly Tyr Asp Asp Ser Glu Gly Val Ile Lys Ala His Asp
225                 230                 235                 240
Ala Glu Asn Leu Ile Tyr Asp Val Thr Phe Glu Val Asp Asp Lys Val
                245                 250                 255
Lys Ser Gly Asp Thr Met Thr Val Asp Ile Asp Lys Asn Thr Val Pro
                260                 265                 270
Ser Asp Leu Thr Asp Ser Phe Thr Ile Pro Lys Ile Lys Asp Asn Ser
                275                 280                 285
Gly Glu Ile Ile Ala Thr Gly Thr Tyr Asp Asn Lys Asn Lys Gln Ile
            290                 295                 300
Thr Tyr Thr Phe Thr Asp Tyr Val Asp Lys Tyr Glu Asn Ile Lys Ala
305                 310                 315                 320
His Leu Lys Leu Thr Ser Tyr Ile Asp Lys Ser Lys Val Pro Asn Asn
                325                 330                 335
Asn Thr Lys Leu Asp Val Glu Tyr Lys Thr Ala Leu Ser Ser Val Asn
                340                 345                 350
Lys Thr Ile Thr Val Glu Tyr Gln Arg Pro Asn Glu Asn Arg Thr Ala
                355                 360                 365
Asn Leu Gln Ser Met Phe Thr Asn Ile Asp Thr Lys Asn His Thr Val
            370                 375                 380
Glu Gln Thr Ile Tyr Ile Asn Pro Leu Arg Tyr Ser Ala Lys Glu Thr
385                 390                 395                 400
Asn Val Asn Ile Ser Gly Asn Gly Asp Glu Gly Ser Thr Ile Ile Asp
                405                 410                 415
Asp Ser Thr Ile Ile Lys Val Tyr Lys Val Gly Asp Asn Gln Asn Leu
                420                 425                 430
Pro Asp Ser Asn Arg Ile Tyr Asp Tyr Ser Glu Tyr Glu Asp Val Thr
                435                 440                 445
Asn Asp Asp Tyr Ala Gln Leu Gly Asn Asn Asp Val Asn Ile Asn
            450                 455                 460
Phe Gly Asn Ile Asp Ser Pro Tyr Ile Lys Val Ile Ser Lys Tyr
465                 470                 475                 480
Asp Pro Asn Lys Asp Asp Tyr Thr Thr Ile Gln Gln Thr Val Thr Met
                485                 490                 495
Gln Thr Thr Ile Asn Glu Tyr Thr Gly Glu Phe Arg Thr Ala Ser Tyr
            500                 505                 510
Asp Asn Thr Ile Ala Phe Ser Ser Ser Gly Gln Gly Gln Gly Asp
            515                 520                 525
Leu Pro Pro Glu Lys Thr Tyr Lys Ile Gly Asp Tyr Val Trp Glu Asp
        530                 535                 540
Val Asp Lys Asp Gly Ile Gln Asn Thr Asn Asp Asn Glu Lys Pro Leu
545                 550                 555                 560
Ser Asn Val Leu Val Thr Leu Thr Tyr Pro Asp Gly Thr Ser Lys Ser
                565                 570                 575
Val Arg Thr Asp Glu Asp Gly Lys Tyr Gln Phe Asp Gly Val Gln Val
                580                 585                 590
Asp
```

<210> SEQ ID NO 12
<211> LENGTH: 1746

<212> TYPE: DNA
<213> ORGANISM: Staphylococcus epidermidis

<400> SEQUENCE: 12

```
tctagtgatg aagaaaagaa tgatgtgatc aataataatc agtcaataaa caccgacgat      60
aataaccaaa taattaaaaa agaagaaacg aataactacg atggcataga aaaacgctca     120
gaagatagaa cagagtcaac aacaaatgta gatgaaaacg aagcaacatt tttacaaaag    180
accccctcaag ataatactca tcttacagaa gaagaggtaa aagaatcctc atcagtcgaa    240
tcctcaaatt catcaattga tactgcccaa caaccatctc acacaacaat aaatagagaa    300
gaatctgttc aaacaagtga taatgtagaa gattcacacg tatcagattt tgctaactct    360
aaaataaaag agagtaacac tgaatctggt aagaagaga atactataga gcaacctaat     420
aaagtaaaag aagattcaac aacaagtcag ccgtctggct atacaaatat agatgaaaaa    480
atttcaaatc aagatgagtt attaaattta ccaataaatg aatatgaaaa taaggctaga    540
ccattatcta caacatctgc ccaaccatcg attaaacgtg taaccgtaaa tcaattagcg    600
gcggaacaag gttcgaatgt taaccattta attaaagtta ctgatcaaag tattactgaa    660
ggatatgatg atagtgaagg tgttattaaa gcacatgatg ctgaaaactt aatctatgat    720
gtaacttttg aagtagatga taaggtgaaa tctggtgata cgatgacagt ggatatagat    780
aagaatacag ttccatcaga tttaaccgat agctttacaa taccaaaaat aaaagataat    840
tctggagaaa tcatcgctac aggtacttat gataacaaaa ataaacaaat cacctatact    900
tttacagatt atgtagataa gtatgaaaat attaaagcac accttaaatt aacgtcatac    960
attgataaat caaaggttcc aaataataat accaagttag atgtagaata taaaacggcc   1020
ctttcatcag taaataaaac aattacggtt gaatatcaaa gacctaacga aaatcggact   1080
gctaaccttc aaagtatgtt tacaaatata gatacgaaaa atcatacagt tgagcaaacg   1140
atttatatta accctcttcg ttattcagcc aaggaaacaa atgtaaatat ttcagggaat   1200
ggtgatgaag gttcaacaat tatagacgat agcacaataa ttaaagttta taaggttgga   1260
gataatcaaa atttaccaga tagtaacaga atttatgatt acagtgaata tgaagatgtc   1320
acaaatgatg attatgccca attaggaaat aataatgatg tgaatattaa ttttggtaat   1380
atagattcac catatattat taaagttatt agtaaatatg accctaataa ggatgattac   1440
acgactatac agcaaactgt gacaatgcag acgactataa atgagtatac tggtgagttt   1500
agaacagcat cctatgataa tacaattgct ttctctacaa gttcaggtca aggacaaggt   1560
gacttgcctc ctgaaaaaac ttataaaatc ggagattacg tatgggaaga tgtagataaa   1620
gatggtattc aaaatacaaa tgataatgaa aaaccgctta gtaatgtatt ggtaactttg   1680
acgtatcctg atggaacttc aaaatcagtc agaacagatg aagatgggaa atatcaattt   1740
gatgga                                                                1746
```

<210> SEQ ID NO 13
<211> LENGTH: 582
<212> TYPE: PRT
<213> ORGANISM: Staphylococcus epidermidis

<400> SEQUENCE: 13

```
Ser Ser Asp Glu Glu Lys Asn Asp Val Ile Asn Asn Asn Gln Ser Ile
 1               5                  10                  15
Asn Thr Asp Asp Asn Asn Gln Ile Ile Lys Lys Glu Glu Thr Asn Asn
            20                  25                  30
```

-continued

```
Tyr Asp Gly Ile Glu Lys Arg Ser Glu Asp Arg Thr Glu Ser Thr Thr
         35                  40                  45

Asn Val Asp Glu Asn Glu Ala Thr Phe Leu Gln Lys Thr Pro Gln Asp
 50                  55                  60

Asn Thr His Leu Thr Glu Glu Val Lys Glu Ser Ser Ser Val Glu
 65                  70                  75                  80

Ser Ser Asn Ser Ser Ile Asp Thr Ala Gln Gln Pro Ser His Thr Thr
                 85                  90                  95

Ile Asn Arg Glu Glu Ser Val Gln Thr Ser Asp Asn Val Glu Asp Ser
             100                 105                 110

His Val Ser Asp Phe Ala Asn Ser Lys Ile Lys Glu Ser Asn Thr Glu
         115                 120                 125

Ser Gly Lys Glu Glu Asn Thr Ile Glu Gln Pro Asn Lys Val Lys Glu
 130                 135                 140

Asp Ser Thr Thr Ser Gln Pro Ser Gly Tyr Thr Asn Ile Asp Glu Lys
145                 150                 155                 160

Ile Ser Asn Gln Asp Glu Leu Leu Asn Leu Pro Ile Asn Glu Tyr Glu
                165                 170                 175

Asn Lys Ala Arg Pro Leu Ser Thr Thr Ser Ala Gln Pro Ser Ile Lys
             180                 185                 190

Arg Val Thr Val Asn Gln Leu Ala Ala Glu Gln Gly Ser Asn Val Asn
         195                 200                 205

His Leu Ile Lys Val Thr Asp Gln Ser Ile Thr Glu Gly Tyr Asp Asp
     210                 215                 220

Ser Glu Gly Val Ile Lys Ala His Asp Ala Glu Asn Leu Ile Tyr Asp
225                 230                 235                 240

Val Thr Phe Glu Val Asp Asp Lys Val Lys Ser Gly Asp Thr Met Thr
                245                 250                 255

Val Asp Ile Asp Lys Asn Thr Val Pro Ser Asp Leu Thr Asp Ser Phe
             260                 265                 270

Thr Ile Pro Lys Ile Lys Asp Asn Ser Gly Glu Ile Ile Ala Thr Gly
         275                 280                 285

Thr Tyr Asp Asn Lys Asn Lys Gln Ile Thr Tyr Thr Phe Thr Asp Tyr
     290                 295                 300

Val Asp Lys Tyr Glu Asn Ile Lys Ala His Leu Lys Leu Thr Ser Tyr
305                 310                 315                 320

Ile Asp Lys Ser Lys Val Pro Asn Asn Asn Thr Lys Leu Asp Val Glu
                325                 330                 335

Tyr Lys Thr Ala Leu Ser Ser Val Asn Lys Thr Ile Thr Val Glu Tyr
             340                 345                 350

Gln Arg Pro Asn Glu Asn Arg Thr Ala Asn Leu Gln Ser Met Phe Thr
         355                 360                 365

Asn Ile Asp Thr Lys Asn His Thr Val Glu Gln Thr Ile Tyr Ile Asn
     370                 375                 380

Pro Leu Arg Tyr Ser Ala Lys Glu Thr Asn Val Asn Ile Ser Gly Asn
385                 390                 395                 400

Gly Asp Glu Gly Ser Thr Ile Ile Asp Asp Ser Thr Ile Ile Lys Val
                405                 410                 415

Tyr Lys Val Gly Asp Asn Gln Asn Leu Pro Asp Ser Asn Arg Ile Tyr
             420                 425                 430

Asp Tyr Ser Glu Tyr Glu Asp Val Thr Asn Asp Tyr Ala Gln Leu
         435                 440                 445

Gly Asn Asn Asn Asp Val Asn Ile Asn Phe Gly Asn Ile Asp Ser Pro
```

```
            450                 455                 460
Tyr Ile Ile Lys Val Ile Ser Lys Tyr Asp Pro Asn Lys Asp Asp Tyr
465                 470                 475                 480

Thr Thr Ile Gln Gln Thr Val Thr Met Gln Thr Thr Ile Asn Glu Tyr
                485                 490                 495

Thr Gly Glu Phe Arg Thr Ala Ser Tyr Asp Asn Thr Ile Ala Phe Ser
            500                 505                 510

Thr Ser Ser Gly Gln Gly Gln Gly Asp Leu Pro Pro Glu Lys Thr Tyr
        515                 520                 525

Lys Ile Gly Asp Tyr Val Trp Glu Asp Val Asp Lys Asp Gly Ile Gln
    530                 535                 540

Asn Thr Asn Asp Asn Glu Lys Pro Leu Ser Asn Val Leu Val Thr Leu
545                 550                 555                 560

Thr Tyr Pro Asp Gly Thr Ser Lys Ser Val Arg Thr Asp Glu Asp Gly
                565                 570                 575

Lys Tyr Gln Phe Asp Gly
                580

<210> SEQ ID NO 14
<211> LENGTH: 3600
<212> TYPE: DNA
<213> ORGANISM: Staphylococcus epidermidis
<220> FEATURE:
<221> NAME/KEY: CDS
<222> LOCATION: (33)..(3308)

<400> SEQUENCE: 14
tacattgaaa tagtcaaaga aaaggagttt tt atg att aat aaa aaa aat aat      53
                                   Met Ile Asn Lys Lys Asn Asn
                                     1               5 tta cta act aaa aag aaa cct ata gca aat aaa tcc aat aaa tat gca     101
Leu Leu Thr Lys Lys Lys Pro Ile Ala Asn Lys Ser Asn Lys Tyr Ala
         10                  15                  20 att aga aaa ttc aca gta ggt aca gcg tct att gta ata ggt gca aca     149
Ile Arg Lys Phe Thr Val Gly Thr Ala Ser Ile Val Ile Gly Ala Thr
     25                  30                  35 tta ttg ttt ggt tta ggt cat aat gag gcc aaa gcc gag gag aat tca     197
Leu Leu Phe Gly Leu Gly His Asn Glu Ala Lys Ala Glu Glu Asn Ser
 40                  45                  50                  55 gta caa gac gtt aaa gat tcg aat acg gat gat gaa tta tca gac agc     245
Val Gln Asp Val Lys Asp Ser Asn Thr Asp Asp Glu Leu Ser Asp Ser
                 60                  65                  70 aat gat cag tct agt gat gaa gaa aag aat gat gtg atc aat aat aat     293
Asn Asp Gln Ser Ser Asp Glu Glu Lys Asn Asp Val Ile Asn Asn Asn
             75                  80                  85 cag tca ata aac acc gac gat aat aac caa ata att aaa aaa gaa gaa     341
Gln Ser Ile Asn Thr Asp Asp Asn Asn Gln Ile Ile Lys Lys Glu Glu
         90                  95                 100 acg aat aac tac gat ggc ata gaa aaa cgc tca gaa gat aga aca gag     389
Thr Asn Asn Tyr Asp Gly Ile Glu Lys Arg Ser Glu Asp Arg Thr Glu
     105                 110                 115 tca aca aca aat gta gat gaa aac gaa gca aca ttt tta caa aag acc     437
Ser Thr Thr Asn Val Asp Glu Asn Glu Ala Thr Phe Leu Gln Lys Thr
120                 125                 130                 135 cct caa gat aat act cat ctt aca gaa gaa gag gta aaa gaa tcc tca     485
Pro Gln Asp Asn Thr His Leu Thr Glu Glu Glu Val Lys Glu Ser Ser
                140                 145                 150 tca gtc gaa tcc tca aat tca tca att gat act gcc caa caa cca tct     533
Ser Val Glu Ser Ser Asn Ser Ser Ile Asp Thr Ala Gln Gln Pro Ser
```

```
                  155                 160                 165
cac aca aca ata aat aga gaa gaa tct gtt caa aca agt gat aat gta    581
His Thr Thr Ile Asn Arg Glu Glu Ser Val Gln Thr Ser Asp Asn Val
            170                 175                 180 gaa gat tca cac gta tca gat ttt gct aac tct aaa ata aaa gag agt    629
Glu Asp Ser His Val Ser Asp Phe Ala Asn Ser Lys Ile Lys Glu Ser
185                 190                 195 aac act gaa tct ggt aaa gaa gag aat act ata gag caa cct aat aaa    677
Asn Thr Glu Ser Gly Lys Glu Glu Asn Thr Ile Glu Gln Pro Asn Lys
200                 205                 210                 215 gta aaa gaa gat tca aca aca agt cag ccg tct ggc tat aca aat ata    725
Val Lys Glu Asp Ser Thr Thr Ser Gln Pro Ser Gly Tyr Thr Asn Ile
                220                 225                 230 gat gaa aaa att tca aat caa gat gag tta tta aat tta cca ata aat    773
Asp Glu Lys Ile Ser Asn Gln Asp Glu Leu Leu Asn Leu Pro Ile Asn
            235                 240                 245 gaa tat gaa aat aag gct aga cca tta tct aca aca tct gcc caa cca    821
Glu Tyr Glu Asn Lys Ala Arg Pro Leu Ser Thr Thr Ser Ala Gln Pro
250                 255                 260 tcg att aaa cgt gta acc gta aat caa tta gcg gcg gaa caa ggt tcg    869
Ser Ile Lys Arg Val Thr Val Asn Gln Leu Ala Ala Glu Gln Gly Ser
265                 270                 275 aat gtt aac cat tta att aaa gtt act gat caa agt att act gaa gga    917
Asn Val Asn His Leu Ile Lys Val Thr Asp Gln Ser Ile Thr Glu Gly
280                 285                 290                 295 tat gat gat agt gaa ggt gtt att aaa gca cat gat gct gaa aac tta    965
Tyr Asp Asp Ser Glu Gly Val Ile Lys Ala His Asp Ala Glu Asn Leu
                300                 305                 310 atc tat gat gta act ttt gaa gta gat gat aag gtg aaa tct ggt gat   1013
Ile Tyr Asp Val Thr Phe Glu Val Asp Asp Lys Val Lys Ser Gly Asp
            315                 320                 325 acg atg aca gtg gat ata gat aag aat aca gtt cca tca gat tta acc   1061
Thr Met Thr Val Asp Ile Asp Lys Asn Thr Val Pro Ser Asp Leu Thr
            330                 335                 340 gat agc ttt aca ata cca aaa ata aaa gat aat tct gga gaa atc atc   1109
Asp Ser Phe Thr Ile Pro Lys Ile Lys Asp Asn Ser Gly Glu Ile Ile
345                 350                 355 gct aca ggt act tat gat aac aaa aat aaa caa atc acc tat act ttt   1157
Ala Thr Gly Thr Tyr Asp Asn Lys Asn Lys Gln Ile Thr Tyr Thr Phe
360                 365                 370                 375 aca gat tat gta gat aag tat gaa aat att aaa gca cac ctt aaa tta   1205
Thr Asp Tyr Val Asp Lys Tyr Glu Asn Ile Lys Ala His Leu Lys Leu
            380                 385                 390 acg tca tac att gat aaa tca aag gtt cca aat aat aat acc aag tta   1253
Thr Ser Tyr Ile Asp Lys Ser Lys Val Pro Asn Asn Asn Thr Lys Leu
            395                 400                 405 gat gta gaa tat aaa acg gcc ctt tca tca gta aat aaa aca att acg   1301
Asp Val Glu Tyr Lys Thr Ala Leu Ser Ser Val Asn Lys Thr Ile Thr
                410                 415                 420 gtt gaa tat caa aga cct aac gaa aat cgg act gct aac ctt caa agt   1349
Val Glu Tyr Gln Arg Pro Asn Glu Asn Arg Thr Ala Asn Leu Gln Ser
            425                 430                 435 atg ttt aca aat ata gat acg aaa aat cat aca gtt gag caa acg att   1397
Met Phe Thr Asn Ile Asp Thr Lys Asn His Thr Val Glu Gln Thr Ile
440                 445                 450                 455 tat att aac cct ctt cgt tat tca gcc aag gaa aca aat gta aat att   1445
Tyr Ile Asn Pro Leu Arg Tyr Ser Ala Lys Glu Thr Asn Val Asn Ile
                460                 465                 470 tca ggg aat ggt gat gaa ggt tca aca att ata gac gat agc aca ata   1493
```

```
Ser Gly Asn Gly Asp Glu Gly Ser Thr Ile Ile Asp Asp Ser Thr Ile
                475                 480                 485 att aaa gtt tat aag gtt gga gat aat caa aat tta cca gat agt aac      1541
Ile Lys Val Tyr Lys Val Gly Asp Asn Gln Asn Leu Pro Asp Ser Asn
            490                 495                 500 aga att tat gat tac agt gaa tat gaa gat gtc aca aat gat gat tat      1589
Arg Ile Tyr Asp Tyr Ser Glu Tyr Glu Asp Val Thr Asn Asp Asp Tyr
        505                 510                 515 gcc caa tta gga aat aat aat gat gtg aat att aat ttt ggt aat ata      1637
Ala Gln Leu Gly Asn Asn Asn Asp Val Asn Ile Asn Phe Gly Asn Ile
520                 525                 530                 535 gat tca cca tat att att aaa gtt att agt aaa tat gac cct aat aag      1685
Asp Ser Pro Tyr Ile Ile Lys Val Ile Ser Lys Tyr Asp Pro Asn Lys
                540                 545                 550 gat gat tac acg act ata cag caa act gtg aca atg cag acg act ata      1733
Asp Asp Tyr Thr Thr Ile Gln Gln Thr Val Thr Met Gln Thr Thr Ile
            555                 560                 565 aat gag tat act ggt gag ttt aga aca gca tcc tat gat aat aca att      1781
Asn Glu Tyr Thr Gly Glu Phe Arg Thr Ala Ser Tyr Asp Asn Thr Ile
        570                 575                 580 gct ttc tct aca agt tca ggt caa gga caa ggt gac ttg cct cct gaa      1829
Ala Phe Ser Thr Ser Ser Gly Gln Gly Gln Gly Asp Leu Pro Pro Glu
585                 590                 595 aaa act tat aaa atc gga gat tac gta tgg gaa gat gta gat aaa gat      1877
Lys Thr Tyr Lys Ile Gly Asp Tyr Val Trp Glu Asp Val Asp Lys Asp
600                 605                 610                 615 ggt att caa aat aca aat gat aat gaa aaa ccg ctt agt aat gta ttg      1925
Gly Ile Gln Asn Thr Asn Asp Asn Glu Lys Pro Leu Ser Asn Val Leu
                620                 625                 630 gta act ttg acg tat cct gat gga act tca aaa tca gtc aga aca gat      1973
Val Thr Leu Thr Tyr Pro Asp Gly Thr Ser Lys Ser Val Arg Thr Asp
            635                 640                 645 gaa gat ggg aaa tat caa ttt gat gga ttg aaa aac gga ttg act tat      2021
Glu Asp Gly Lys Tyr Gln Phe Asp Gly Leu Lys Asn Gly Leu Thr Tyr
        650                 655                 660 aaa att aca ttc gaa aca cct gaa gga tat acg ccg acg ctt aaa cat      2069
Lys Ile Thr Phe Glu Thr Pro Glu Gly Tyr Thr Pro Thr Leu Lys His
665                 670                 675 tca gga aca aat cct gca cta gac tca gaa ggt aat tct gta tgg gta      2117
Ser Gly Thr Asn Pro Ala Leu Asp Ser Glu Gly Asn Ser Val Trp Val
680                 685                 690                 695 act att aat gga caa gac gat atg acg att gat agt gga ttt tat caa      2165
Thr Ile Asn Gly Gln Asp Asp Met Thr Ile Asp Ser Gly Phe Tyr Gln
                700                 705                 710 aca cct aaa tac agc tta ggg aac tat gta tgg tat gac act aat aaa      2213
Thr Pro Lys Tyr Ser Leu Gly Asn Tyr Val Trp Tyr Asp Thr Asn Lys
            715                 720                 725 gat ggt att caa ggt gat gat gaa aaa gga atc tct gga gtt aaa gtg      2261
Asp Gly Ile Gln Gly Asp Asp Glu Lys Gly Ile Ser Gly Val Lys Val
        730                 735                 740 acg tta aaa gat gaa aac gga aat atc att agt aca act aca acc gat      2309
Thr Leu Lys Asp Glu Asn Gly Asn Ile Ile Ser Thr Thr Thr Thr Asp
745                 750                 755 gaa aat gga aag tat caa ttt gat aat tta aat agt ggt aat tat att      2357
Glu Asn Gly Lys Tyr Gln Phe Asp Asn Leu Asn Ser Gly Asn Tyr Ile
760                 765                 770                 775 gtt cat ttt gat aaa cct tca ggt atg act caa aca aca aca gat tct      2405
Val His Phe Asp Lys Pro Ser Gly Met Thr Gln Thr Thr Thr Asp Ser
                780                 785                 790
```

```
ggt gat gat gac gaa cag gat gct gat ggg gaa gaa gtt cat gta aca    2453
Gly Asp Asp Asp Glu Gln Asp Ala Asp Gly Glu Glu Val His Val Thr
            795                 800                 805 att act gat cat gat gac ttt agt ata gat aac gga tac tat gat gac    2501
Ile Thr Asp His Asp Asp Phe Ser Ile Asp Asn Gly Tyr Tyr Asp Asp
810                 815                 820 gaa tcg gat tcc gat agt gac tca gac agc gac tca gat tcc gat agt    2549
Glu Ser Asp Ser Asp Ser Asp Ser Asp Ser Asp Ser Asp Ser Asp Ser
    825                 830                 835 gat tca gac tcc gat agc gac tcg gat tca gac agc gac tca gat tca    2597
Asp Ser Asp Ser Asp Ser Asp Ser Asp Ser Asp Ser Asp Ser Asp Ser
840                 845                 850                 855 gac agc gac tcg gat tct gat agc gac tcg gat tca gac agc gac tca    2645
Asp Ser Asp Ser Asp Ser Asp Ser Asp Ser Asp Ser Asp Ser Asp Ser
                860                 865                 870 gac tca gac agt gat tca gat tca gac agc gac tca gat tcc gat agt    2693
Asp Ser Asp Ser Asp Ser Asp Ser Asp Ser Asp Ser Asp Ser Asp Ser
    875                 880                 885 gat tca gac tca gac agc gac tca gat tct gat agt gat tca gac tca    2741
Asp Ser Asp Ser Asp Ser Asp Ser Asp Ser Asp Ser Asp Ser Asp Ser
890                 895                 900 gac agt gat tca gat tca gac agc gac tca gat tcc gat agt gat tca    2789
Asp Ser Asp Ser Asp Ser Asp Ser Asp Ser Asp Ser Asp Ser Asp Ser
    905                 910                 915 gac tca gac agc gac tca gat tcc gat agt gat tca gac tca gac agc    2837
Asp Ser Asp Ser Asp Ser Asp Ser Asp Ser Asp Ser Asp Ser Asp Ser
920                 925                 930                 935 gac tca gat tct gat agt gat tca gac tca gac agt gat tca gac tca    2885
Asp Ser Asp Ser Asp Ser Asp Ser Asp Ser Asp Ser Asp Ser Asp Ser
                940                 945                 950 gac agt gat tca gat tcc gat agt gat tca gac tcc gat agc gac tca    2933
Asp Ser Asp Ser Asp Ser Asp Ser Asp Ser Asp Ser Asp Ser Asp Ser
    955                 960                 965 gac tcg gat agt gac tca gat tct gat agt gat tca gac tcc gat agc    2981
Asp Ser Asp Ser Asp Ser Asp Ser Asp Ser Asp Ser Asp Ser Asp Ser
970                 975                 980 gac tca gac tcg gat agt gac tca gat tct gat agt gat tca gac tca    3029
Asp Ser Asp Ser Asp Ser Asp Ser Asp Ser Asp Ser Asp Ser Asp Ser
    985                 990                 995 gac agc gac tca gat tct gat agt gat tca gac tca gtc agt gat tca    3077
Asp Ser Asp Ser Asp Ser Asp Ser Asp Ser Asp Ser Val Ser Asp Ser
1000                1005                1010                1015 gat tcc gat agt gat tca gac tca ggc agt gat tcg gat tcc gat agt    3125
Asp Ser Asp Ser Asp Ser Asp Ser Gly Ser Asp Ser Asp Ser Asp Ser
                1020                1025                1030 gat tca gac tca gac aac gac tca gat tta ggc aat agc tca gat aag    3173
Asp Ser Asp Ser Asp Asn Asp Ser Asp Leu Gly Asn Ser Ser Asp Lys
    1035                1040                1045 agt aca aaa gat aaa tta cct gat aca gga gct aat gaa gat tat ggc    3221
Ser Thr Lys Asp Lys Leu Pro Asp Thr Gly Ala Asn Glu Asp Tyr Gly
1050                1055                1060 tct aaa ggc acg tta ctt gga act ctg ttt gca ggt tta gga gcg tta    3269
Ser Lys Gly Thr Leu Leu Gly Thr Leu Phe Ala Gly Leu Gly Ala Leu
    1065                1070                1075 tta tta ggg aaa cgt cgc aaa aat aga aaa aat aaa aat taaaatgttc     3318
Leu Leu Gly Lys Arg Arg Lys Asn Arg Lys Asn Lys Asn
1080                1085                1090 aaatgaaatt tgtagaaaga agcagatatg agatttgaat agaaagtaga tttagtccaa  3378
caaatgtaag atgttgatta aaactataat ataactttca cgtttatcat atcttgtgaa  3438
```

-continued

```
aaagatgatg caaacaaggt catttctatt aaaaatgact taaatgtatg attttagag    3498 aaacatatac aactcacaat ctgacaatga tttaatagag gaaccgtgaa ttttaaatga   3558
attcatggtt cctttttatt gaattaataa aaattctttt at                     3600
```

<210> SEQ ID NO 15
<211> LENGTH: 1092
<212> TYPE: PRT
<213> ORGANISM: Staphylococcus epidermidis

<400> SEQUENCE: 15

```
Met Ile Asn Lys Lys Asn Asn Leu Leu Thr Lys Lys Pro Ile Ala
 1               5                  10                  15

Asn Lys Ser Asn Lys Tyr Ala Ile Arg Lys Phe Thr Val Gly Thr Ala
                20                  25                  30

Ser Ile Val Ile Gly Ala Thr Leu Leu Phe Gly Leu Gly His Asn Glu
            35                  40                  45

Ala Lys Ala Glu Glu Asn Ser Val Gln Asp Val Lys Asp Ser Asn Thr
        50                  55                  60

Asp Asp Glu Leu Ser Asp Ser Asn Asp Gln Ser Ser Asp Glu Glu Lys
 65                 70                  75                  80

Asn Asp Val Ile Asn Asn Gln Ser Ile Asn Thr Asp Asp Asn Asn
                85                  90                  95

Gln Ile Ile Lys Lys Glu Glu Thr Asn Asn Tyr Asp Gly Ile Glu Lys
                100                 105                 110

Arg Ser Glu Asp Arg Thr Glu Ser Thr Thr Asn Val Asp Glu Asn Glu
            115                 120                 125

Ala Thr Phe Leu Gln Lys Thr Pro Gln Asp Asn Thr His Leu Thr Glu
        130                 135                 140

Glu Glu Val Lys Glu Ser Ser Ser Val Glu Ser Ser Asn Ser Ser Ile
145                 150                 155                 160

Asp Thr Ala Gln Gln Pro Ser His Thr Thr Ile Asn Arg Glu Glu Ser
                165                 170                 175

Val Gln Thr Ser Asp Asn Val Glu Asp Ser His Val Ser Asp Phe Ala
            180                 185                 190

Asn Ser Lys Ile Lys Glu Ser Asn Thr Glu Ser Gly Lys Glu Glu Asn
        195                 200                 205

Thr Ile Glu Gln Pro Asn Lys Val Lys Glu Asp Ser Thr Thr Ser Gln
    210                 215                 220

Pro Ser Gly Tyr Thr Asn Ile Asp Glu Lys Ile Ser Asn Gln Asp Glu
225                 230                 235                 240

Leu Leu Asn Leu Pro Ile Asn Glu Tyr Glu Asn Lys Ala Arg Pro Leu
                245                 250                 255

Ser Thr Thr Ser Ala Gln Pro Ser Ile Lys Arg Val Thr Val Asn Gln
            260                 265                 270

Leu Ala Ala Glu Gln Gly Ser Asn Val Asn His Leu Ile Lys Val Thr
        275                 280                 285

Asp Gln Ser Ile Thr Glu Gly Tyr Asp Asp Ser Glu Gly Val Ile Lys
    290                 295                 300

Ala His Asp Ala Glu Asn Leu Ile Tyr Asp Val Thr Phe Glu Val Asp
305                 310                 315                 320

Asp Lys Val Lys Ser Gly Asp Thr Met Thr Val Asp Ile Asp Lys Asn
                325                 330                 335

Thr Val Pro Ser Asp Leu Thr Asp Ser Phe Thr Ile Pro Lys Ile Lys
```

-continued

```
                340                 345                 350
Asp Asn Ser Gly Glu Ile Ile Ala Thr Gly Thr Tyr Asp Asn Lys Asn
            355                 360                 365
Lys Gln Ile Thr Tyr Thr Phe Thr Asp Tyr Val Asp Lys Tyr Glu Asn
        370                 375                 380
Ile Lys Ala His Leu Lys Leu Thr Ser Tyr Ile Asp Lys Ser Lys Val
385                 390                 395                 400
Pro Asn Asn Thr Lys Leu Asp Val Glu Tyr Lys Thr Ala Leu Ser
            405                 410                 415
Ser Val Asn Lys Thr Ile Thr Val Glu Tyr Gln Arg Pro Asn Glu Asn
            420                 425                 430
Arg Thr Ala Asn Leu Gln Ser Met Phe Thr Asn Ile Asp Thr Lys Asn
        435                 440                 445
His Thr Val Glu Gln Thr Ile Tyr Ile Asn Pro Leu Arg Tyr Ser Ala
        450                 455                 460
Lys Glu Thr Asn Val Asn Ile Ser Gly Asn Gly Asp Glu Gly Ser Thr
465                 470                 475                 480
Ile Ile Asp Asp Ser Thr Ile Ile Lys Val Tyr Lys Val Gly Asp Asn
            485                 490                 495
Gln Asn Leu Pro Asp Ser Asn Arg Ile Tyr Asp Tyr Ser Glu Tyr Glu
            500                 505                 510
Asp Val Thr Asn Asp Asp Tyr Ala Gln Leu Gly Asn Asn Asn Asp Val
        515                 520                 525
Asn Ile Asn Phe Gly Asn Ile Asp Ser Pro Tyr Ile Ile Lys Val Ile
        530                 535                 540
Ser Lys Tyr Asp Pro Asn Lys Asp Asp Tyr Thr Thr Ile Gln Gln Thr
545                 550                 555                 560
Val Thr Met Gln Thr Thr Ile Asn Glu Tyr Thr Gly Glu Phe Arg Thr
            565                 570                 575
Ala Ser Tyr Asp Asn Thr Ile Ala Phe Ser Thr Ser Ser Gly Gln Gly
        580                 585                 590
Gln Gly Asp Leu Pro Pro Glu Lys Thr Tyr Lys Ile Gly Asp Tyr Val
        595                 600                 605
Trp Glu Asp Val Asp Lys Asp Gly Ile Gln Asn Thr Asn Asp Asn Glu
        610                 615                 620
Lys Pro Leu Ser Asn Val Leu Val Thr Leu Thr Tyr Pro Asp Gly Thr
625                 630                 635                 640
Ser Lys Ser Val Arg Thr Asp Glu Asp Gly Lys Tyr Gln Phe Asp Gly
            645                 650                 655
Leu Lys Asn Gly Leu Thr Tyr Lys Ile Thr Phe Glu Thr Pro Glu Gly
            660                 665                 670
Tyr Thr Pro Thr Leu Lys His Ser Gly Thr Asn Pro Ala Leu Asp Ser
        675                 680                 685
Glu Gly Asn Ser Val Trp Val Thr Ile Asn Gly Gln Asp Asp Met Thr
        690                 695                 700
Ile Asp Ser Gly Phe Tyr Gln Thr Pro Lys Tyr Ser Leu Gly Asn Tyr
705                 710                 715                 720
Val Trp Tyr Asp Thr Asn Lys Asp Gly Ile Gln Gly Asp Glu Lys
            725                 730                 735
Gly Ile Ser Gly Val Lys Val Thr Leu Lys Asp Glu Asn Gly Asn Ile
            740                 745                 750
Ile Ser Thr Thr Thr Thr Asp Glu Asn Gly Lys Tyr Gln Phe Asp Asn
        755                 760                 765
```

```
Leu Asn Ser Gly Asn Tyr Ile Val His Phe Asp Lys Pro Ser Gly Met
    770             775                 780
Thr Gln Thr Thr Thr Asp Ser Gly Asp Asp Asp Glu Gln Asp Ala Asp
785             790                 795                 800
Gly Glu Glu Val His Val Thr Ile Thr Asp His Asp Asp Phe Ser Ile
                805                 810                 815
Asp Asn Gly Tyr Tyr Asp Asp Glu Ser Asp Ser Asp Ser Asp Ser Asp
            820                 825                 830
Ser Asp Ser Asp Ser Asp Ser Asp Ser Asp Ser Asp Ser Asp Ser Asp
        835                 840                 845
Ser Asp Ser Asp Ser Asp Ser Asp Ser Asp Ser Asp Ser Asp Ser Asp
850                 855                 860
Ser Asp Ser Asp Ser Asp Ser Asp Ser Asp Ser Asp Ser Asp Ser Asp
865                 870                 875                 880
Ser Asp Ser Asp Ser Asp Ser Asp Ser Asp Ser Asp Ser Asp Ser Asp
            885                 890                 895
Ser Asp Ser Asp Ser Asp Ser Asp Ser Asp Ser Asp Ser Asp Ser Asp
        900                 905                 910
Ser Asp Ser Asp Ser Asp Ser Asp Ser Asp Ser Asp Ser Asp Ser Asp
    915                 920                 925
Ser Asp Ser Asp Ser Asp Ser Asp Ser Asp Ser Asp Ser Asp Ser Asp
    930                 935                 940
Ser Asp Ser Asp Ser Asp Ser Asp Ser Asp Ser Asp Ser Asp Ser Asp
945                 950                 955                 960
Ser Asp Ser Asp Ser Asp Ser Asp Ser Asp Ser Asp Ser Asp Ser Asp
            965                 970                 975
Ser Asp Ser Asp Ser Asp Ser Asp Ser Asp Ser Asp Ser Asp Ser Asp
            980                 985                 990
Ser Asp Ser Asp Ser Asp Ser Asp Ser Asp Ser Asp Ser Asp Ser Asp
        995                 1000                1005
Ser Asp Ser Val Ser Asp Ser Asp Ser Asp Ser Asp Ser Asp Ser Gly
    1010                1015                1020
Ser Asp Ser Asp Ser Asp Ser Asp Ser Asp Ser Asp Asn Asp Ser Asp
1025                1030                1035                1040
Leu Gly Asn Ser Ser Asp Lys Ser Thr Lys Asp Lys Leu Pro Asp Thr
                1045                1050                1055
Gly Ala Asn Glu Asp Tyr Gly Ser Lys Gly Thr Leu Leu Gly Thr Leu
            1060                1065                1070
Phe Ala Gly Leu Gly Ala Leu Leu Leu Gly Lys Arg Arg Lys Asn Arg
        1075                1080                1085
Lys Asn Lys Asn
    1090
```